(12) United States Patent
Bull et al.

(10) Patent No.: US 8,524,749 B2
(45) Date of Patent: Sep. 3, 2013

(54) CONTROLLED RELEASE COMPOSITIONS OF TIZANIDINE

(75) Inventors: Scott Bull, Danville, CA (US); Suneel Gupta, Sunnyvale, CA (US); Rhea Donley, Campbell, CA (US); Nishit Modi, Sunnyvale, CA (US); Noymi Yam, Sunnyvale, CA (US)

(73) Assignee: ALZA Corporation, Vacaville, CA (US)

( * ) Notice: Subject to any disclaimer, the term of this patent is extended or adjusted under 35 U.S.C. 154(b) by 756 days.

(21) Appl. No.: 12/014,980

(22) Filed: Jan. 16, 2008

(65) Prior Publication Data

US 2008/0214629 A1    Sep. 4, 2008

Related U.S. Application Data

(60) Provisional application No. 60/889,023, filed on Feb. 9, 2007.

(51) Int. Cl.
*A61K 31/433* (2006.01)
*A61P 21/00* (2006.01)

(52) U.S. Cl.
USPC .......................................... 514/362

(58) Field of Classification Search
None
See application file for complete search history.

(56) References Cited

U.S. PATENT DOCUMENTS

| | | | |
|---|---|---|---|
| 2,799,241 A | 7/1957 | Wurster | |
| 3,133,132 A | 5/1964 | Sidney et al. | |
| 3,173,876 A | 3/1965 | Zobrist | |
| 3,276,586 A | 10/1966 | Rosaen | |
| 3,541,005 A | 11/1970 | Strathmann et al. | |
| 3,541,006 A | 11/1970 | Bixler et al. | |
| 3,546,142 A | 12/1970 | Michaels et al. | |
| 3,843,668 A | 10/1974 | Neumann | |
| 3,845,770 A | 11/1974 | Theeuwes et al. | |
| 3,865,108 A | 2/1975 | Hartop | |
| 3,916,899 A | 11/1975 | Theeuwes et al. | |
| 3,995,631 A | 12/1976 | Higuchi et al. | |
| 4,002,173 A | 1/1977 | Manning et al. | |
| 4,008,719 A | 2/1977 | Theeuwes et al. | |
| 4,053,617 A | 10/1977 | Eichenberger et al. | |
| 4,077,407 A | 3/1978 | Theeuwes et al. | |
| 4,088,864 A | 5/1978 | Theeuwes et al. | |
| 4,111,202 A | 9/1978 | Theeuwes | |
| 4,160,020 A | 7/1979 | Ayer et al. | |
| 4,200,098 A | 4/1980 | Ayer et al. | |
| 4,207,893 A | 6/1980 | Michaels | |
| 4,327,725 A | 5/1982 | Cortese et al. | |
| 4,578,075 A | 3/1986 | Urquhart et al. | |
| 4,627,850 A | 12/1986 | Deters et al. | |
| 4,663,148 A | 5/1987 | Eckenhoff et al. | |
| 4,681,583 A | 7/1987 | Urquhart et al. | |
| 4,783,337 A | 11/1988 | Wong et al. | |
| 4,915,949 A | 4/1990 | Wong et al. | |
| 4,931,285 A | 6/1990 | Edgren et al. | |
| 5,006,346 A | 4/1991 | Edgren et al. | |
| 5,019,397 A | 5/1991 | Wong et al. | |
| 5,024,842 A | 6/1991 | Edgren et al. | |
| 5,126,142 A | 6/1992 | Ayer et al. | |
| 5,156,850 A | 10/1992 | Wong et al. | |
| 5,160,743 A | 11/1992 | Edgren et al. | |
| 5,190,765 A | 3/1993 | Jao et al. | |
| 5,252,338 A | 10/1993 | Jao et al. | |
| 5,324,280 A | 6/1994 | Wong et al. | |
| 5,614,578 A | 3/1997 | Dong et al. | |
| 5,620,705 A | 4/1997 | Dong et al. | |
| 5,633,011 A | 5/1997 | Dong et al. | |
| 5,660,861 A | 8/1997 | Jao et al. | |
| 6,174,547 B1 | 1/2001 | Dong et al. | |
| 6,419,952 B2 | 7/2002 | Wong et al. | |
| 6,596,314 B2 | 7/2003 | Wong et al. | |
| 2004/0092534 A1* | 5/2004 | Yam et al. | 514/259.41 |
| 2005/0008702 A1* | 1/2005 | Faour et al. | 424/473 |
| 2005/0053653 A1* | 3/2005 | Kidane et al. | 424/463 |
| 2007/0078174 A1* | 4/2007 | Flashner-Barak et al. | 514/363 |

FOREIGN PATENT DOCUMENTS

WO    2008/008394    * 1/2008

OTHER PUBLICATIONS

Galinsky et al., "Basic Pharmacokinetics and Pharmacodynamics," chapter 58, in Remington's The Science and Practice of Pharmacy, p. 1171 (2006).*
Chemical Engineer, Hixon, pp. 94-103 (1990).
Chemical Engineers Handbook, Perry, $6^{th}$ Ed., pp. 21-19 (1984).
Encyclopedia of Polymer Science and Technology, vol. 3, pp. 325-354, 1964, published by Interscience Publishers, Inc., New York.
J. Am. Pharm. Assoc., vol. 48, pp. 451-459 (1959).
J. Am. Pharm. Assoc., vol. 49, pp. 82-84 (1960).
Journal of Pharmaceutical Sciences, Parrot, vol. 61, No. 6, pp. 813-829 (1974).
Pharmaceutical Sciences, Remington, $17^{th}$ Ed., pp. 1585-1594 (1985).
Pharmaceutical Sciences, Remington, $18^{th}$ Ed., pp. 1676-1686 (1990), Mack Publishing Co.
Remington's Pharmaceutical Sciences, 1990 ed., pp. 1682-1685.
Santus and Baker, "Osmotic drug delivery: a review of the patent literature," Journal of Controlled Release 35 (1995) pp. 1-21.
Gibaldi, M., Biopharmaceutics and Clinical Pharmacokinetics, $3^{rd}$ Ed., pp. 1-28 (1984), Lea and Febreger, Philadelphia.

* cited by examiner

*Primary Examiner* — Suzanne Ziska
(74) *Attorney, Agent, or Firm* — Kiera K. Mathey

(57) ABSTRACT

The present invention relates to a novel controlled release formulations of tizanidine. The invention also provides methods of using novel controlled release formulations of tizanidine to treat a patient.

12 Claims, 9 Drawing Sheets

FIG. 3    Release rates of the ascending profile controlled release tizanidine (n = 10)
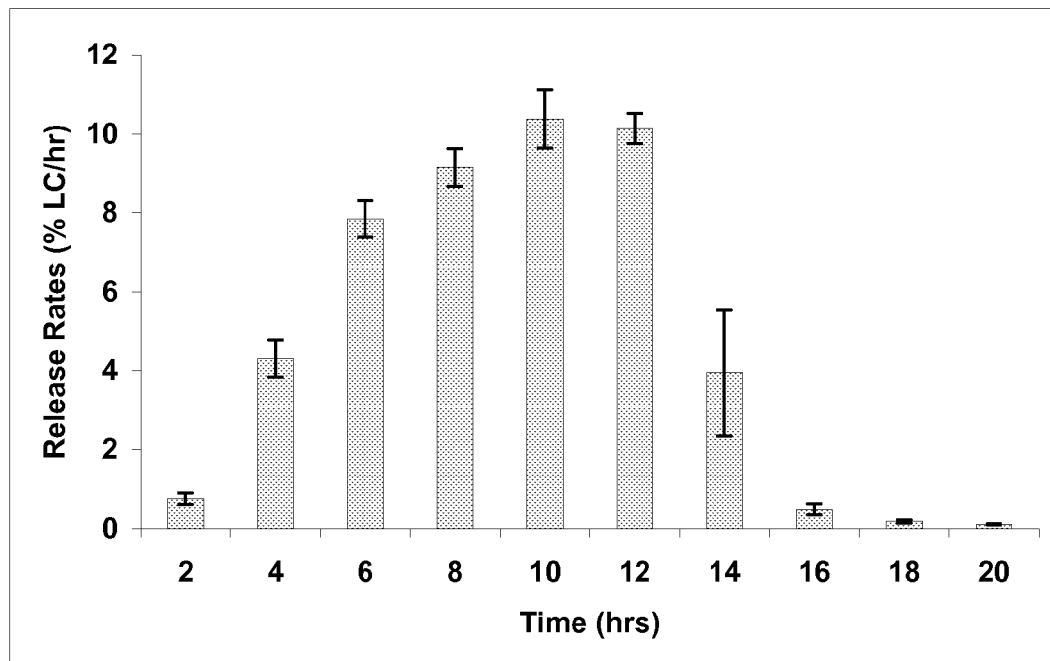

FIG. 4    Effect of tizanidine salt form on release profile
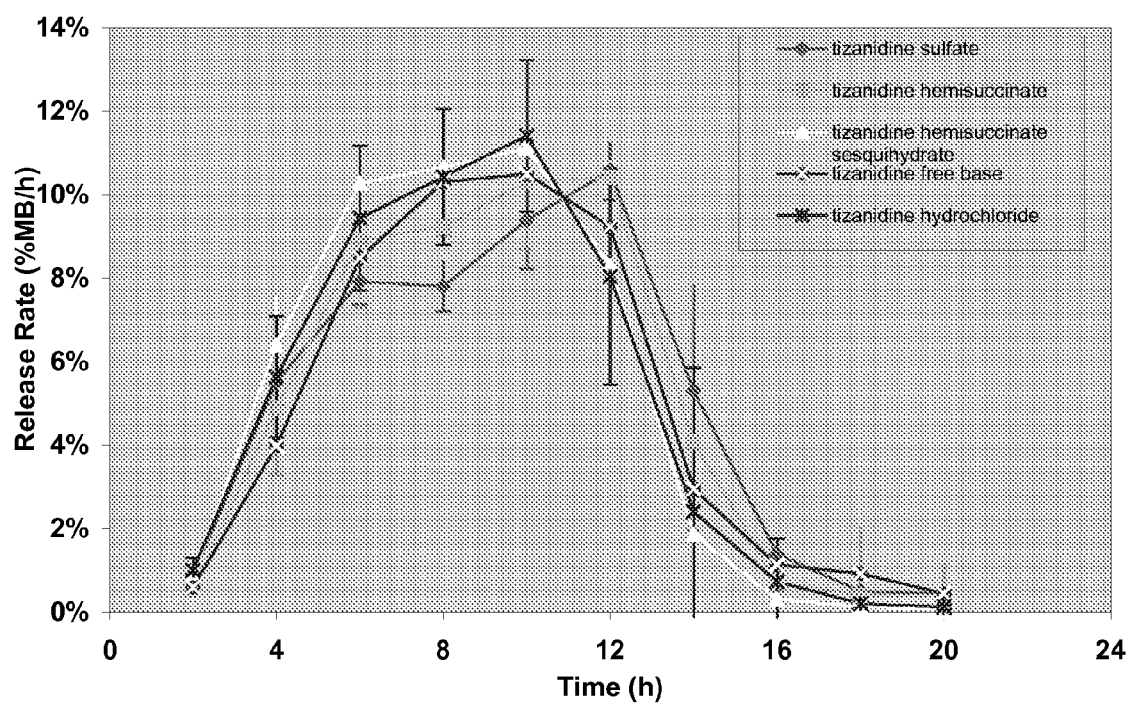

FIG. 5  Mean Tizanidine Plasma Concentration-Time Profiles for Immediate-Release (IR) and Controlled Release Formulations
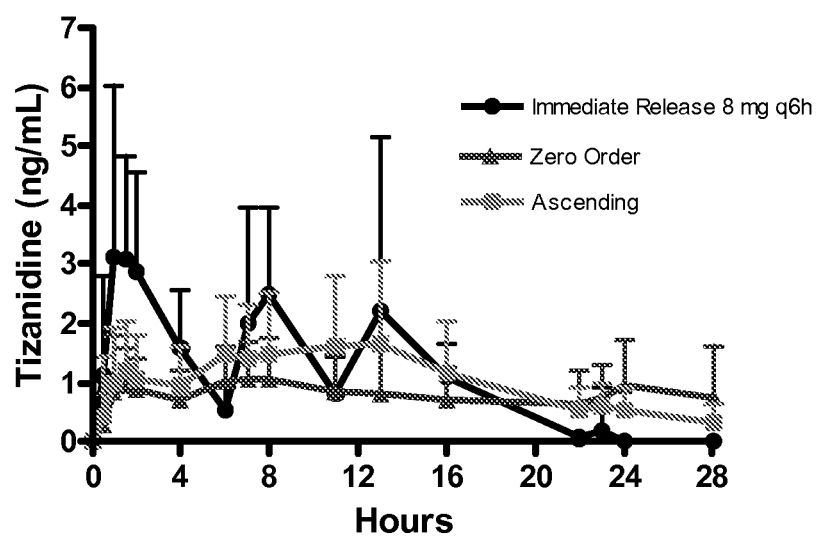

FIG. 6  Effect of Various Tizanidine Formulations on Karolinska Sleepiness Scale (KSS)
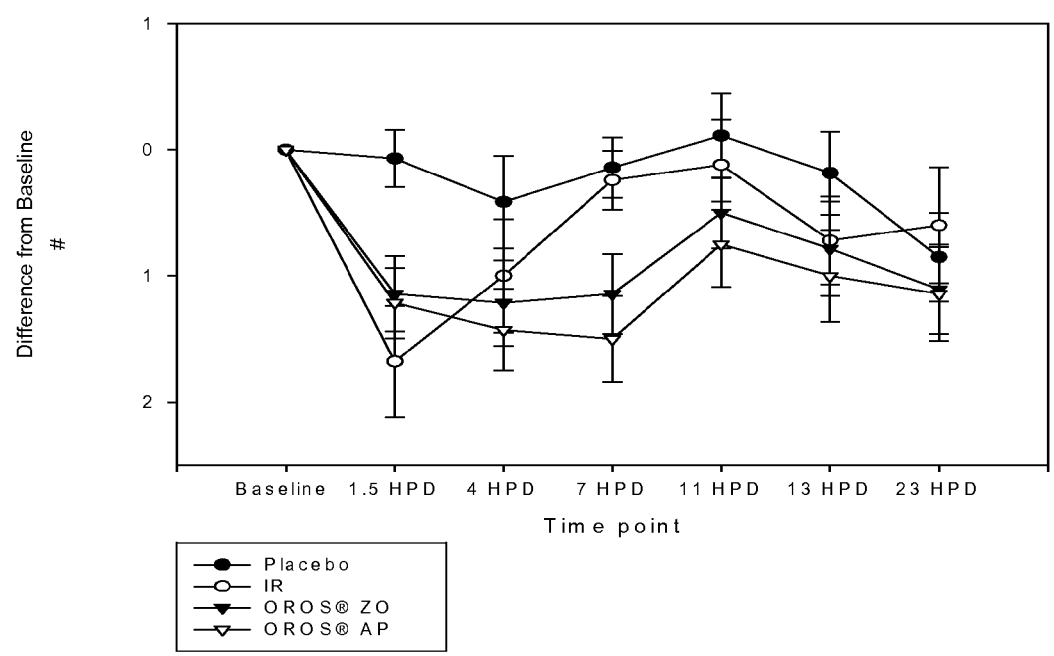

FIG. 7    Effect of Various Tizanidine Formulations on Power of Attention Composite Score
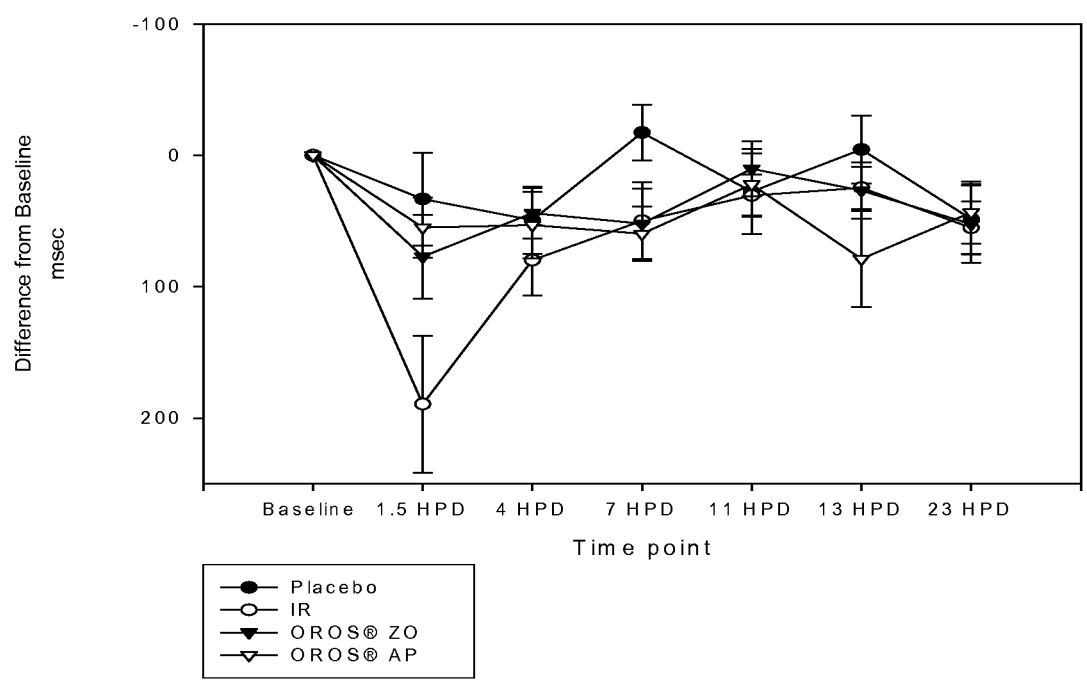

FIG. 8  Effect of Various Tizanidine Formulations on Continuity of Attention Composite Score
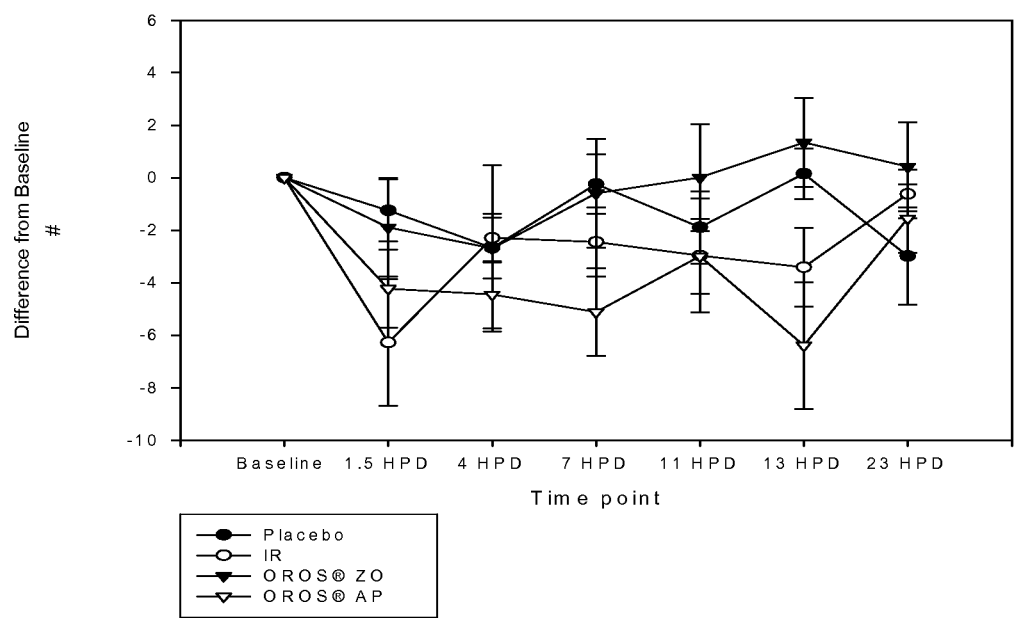

FIG. 9  Effect of Alcohol on the Peak Impairment in Power of Attention
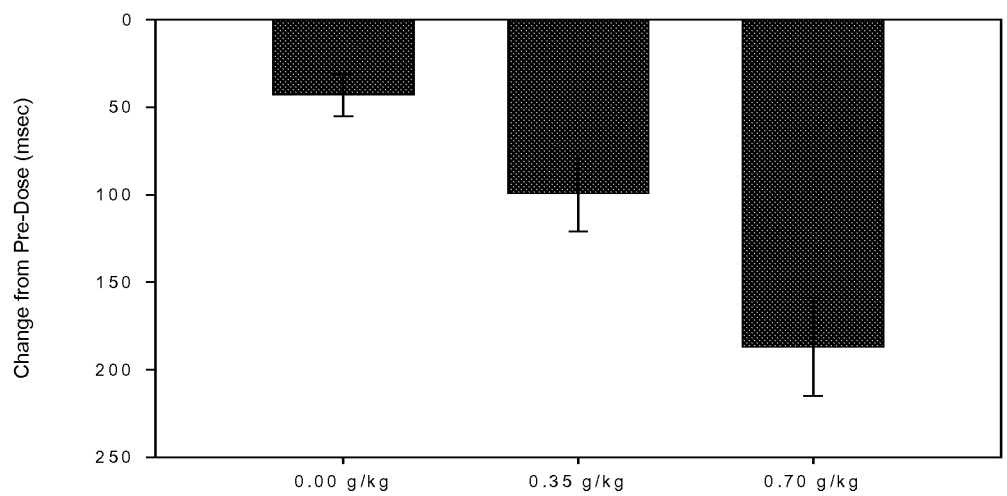

CONTROLLED RELEASE COMPOSITIONS OF TIZANIDINE

FIELD OF THE INVENTION

The present invention relates to a novel controlled release formulations of tizanidine. The invention also provides methods of using novel controlled release formulations of tizanidine to treat a patient.

BACKGROUND OF THE INVENTION

Tizanidine is pharmacologically characterized as a central-acting α2 adrenoceptor agonist which has various pharmacological activities. The imidazoline chemical structure of tizanidine is related to other α2-adrenergic agonists.

Tizanidine can be classified generically as an amino-imidazoline adrenergic agent. In chemical nomenclature the molecule is described as 5-chloro-4-(2-imidazolin-2-ylamino)-2,1,3-benzothiadiazole and is also identified with Chemical Abstracts Registry number 51322-75-9. Synthesis of the compound is disclosed in U.S. Pat. Nos. 3,843,668 and 4,053,617. Tizanidine hydrochloride is currently approved by the US Food and Drug Administration for the treatment of spasticity.

Presently, an immediate release formulation of tizanidine hydrochloride is dosed orally up to three times a day. This frequent oral dosing may lead to large fluctuations in the release profile of tizanidine hydrochloride, and subsequently, large fluctuations in the blood serum concentration of tizanidine. Side effects of immediate release tizanidine hydrochloride, such as somnolence, may be related to either the fluctuations in tizanidine concentration or excessively high tizanidine concentration, or both. A modified release formulation of tizanidine hydrochloride is approved in some European countries, but this modified release tizanidine hydrochloride has not shown any significant reduction in tizanidine hydrochloride side effects. A controlled release formulation of tizanidine should enable better command over the release profile and consequently, the blood serum concentration of tizanidine. While simply reformulating tizanidine in a modified release formulation has failed to achieve a significant reduction in side effects, applicants have discovered formulations and methods which tailor the tizanidine dose to reduce side effects.

BRIEF SUMMARY OF THE INVENTION

In one embodiment, the invention comprises a method of treating a patient suffering from spasticity, multiple sclerosis, or amyotrophic lateral sclerosis, wherein said method comprises administering a dosage form comprising 6-20 mg of tizanidine wherein said tizanidine is released in manner such that tizanidine plasma drug concentration substantially ascends over a period of 8 hours following administration. In one embodiment, a pharmaceutical composition comprises a first layer of tizanidine and a second layer of tizanidine wherein said first layer is substantially released within 3 hours of administration and said second layer of tizanidine is substantially released over a period of 1-14 hours. In another embodiment, a pharmaceutical composition comprises a first layer of tizanidine and a second layer of tizanidine wherein said first layer is substantially released within 3 hours of administration and said second layer of tizanidine is substantially released over a period of 1-12 hours and wherein said pharmaceutical composition is in the form of an osmotic drug delivery system. In another embodiment, a pharmaceutical composition comprises a first layer of tizanidine of tizanidine and a second layer of tizanidine of tizanidine wherein said administration of said pharmaceutical composition results in patient peak plasma blood levels of between 1-4 ng/ml between 3-12 hours after administration. In another embodiment, the invention comprises a method of treating a condition which is responsive to tizanidine, the method comprising orally administering a tizanidine dosage form that produces a substantially increasing plasma tizanidine concentration following dosage administration.

BRIEF DESCRIPTION OF THE DRAWINGS

FIG. 3: Release rates of the ascending profile controlled release tizanidine (n=10).
FIG. 4: Effect of tizanidine salt form on release profile.
FIG. 5: Mean Tizanidine Plasma Concentration-Time Profiles for Immediate-Release (IR) and Controlled Release Formulations.
FIG. 6: Effect of Various Tizanidine Formulations on Karolinska Sleepiness Scale (KSS).
FIG. 7: Effect of Various Tizanidine Formulations on Power of Attention Composite Score.
FIG. 8: Effect of Various Tizanidine Formulations on Continuity of Attention Composite Score.
FIG. 9: Effect of Alcohol on the Peak Impairment in Power of Attention.

DETAILED DESCRIPTION OF THE INVENTION

Figure 1:
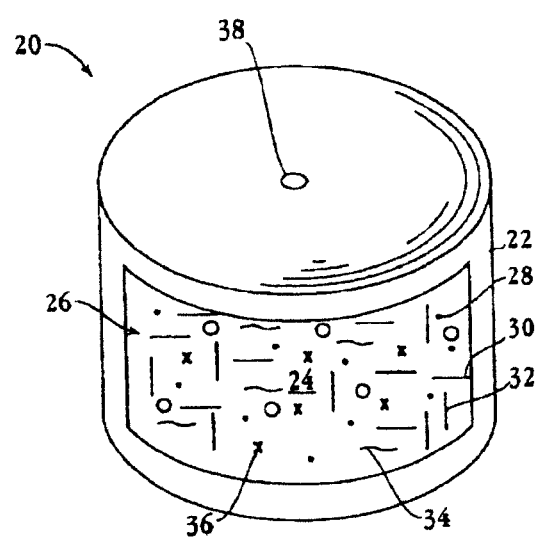
FIG. 1: An exemplary osmotic delivery device.

In one embodiment, the invention comprises a method of treating a patient suffering from spasticity, multiple sclerosis, or amyotrophic lateral sclerosis, wherein said method comprises administering a dosage form comprising 6-20 mg of tizanidine wherein said tizanidine is released in manner such that tizanidine plasma drug concentration substantially ascends over a period of 8 hours following administration. In another embodiment, the invention comprises a method of treating a patient suffering from spasticity, multiple sclerosis, or amyotrophic lateral sclerosis, wherein said method comprises administering a dosage form comprising 6-20 mg of tizanidine wherein said tizanidine is released in manner such that tizanidine plasma drug concentration substantially ascends over a period of 10 hours following administration. In another embodiment, the invention comprises a method of treating a patient suffering from spasticity, multiple sclerosis, or amyotrophic lateral sclerosis, wherein said method comprises administering a dosage form comprising 6-20 mg of tizanidine wherein said tizanidine is released in manner such that tizanidine plasma drug concentration substantially ascends over a period of 12 hours following administration. In another embodiment, the invention comprises a method of treating a patient suffering from spasticity, multiple sclerosis, or amyotrophic lateral sclerosis, wherein said method comprises administering a dosage form comprising 6-20 mg of tizanidine wherein said tizanidine is released in manner such that tizanidine plasma drug concentration substantially ascends over a period of 8 hours following administration and where the peak plasma blood concentration of tizanidine is between 1-4 ng/ml. In another embodiment, the invention comprises a method of treating a patient suffering from spasticity, multiple sclerosis, or amyotrophic lateral sclerosis, wherein said method comprises administering a dosage form comprising 6-20 mg of tizanidine wherein said tizanidine is released in manner such that tizanidine plasma drug concentration substantially ascends over a period of 10 hours following administration and where the peak plasma blood concentration of tizanidine is between 1-4 ng/ml. In another embodiment, the invention comprises a method of treating a patient suffering from spasticity, multiple sclerosis, or amyotrophic lateral sclerosis, wherein said method comprises administering a dosage form comprising 6-20 mg of tizanidine wherein said tizanidine is released in manner such that tizanidine plasma drug concentration substantially ascends over a period of 8 hours following administration and where the peak plasma blood concentration of tizanidine is between 1.6-3.2 ng/ml. In another embodiment, the invention comprises a method of treating a patient suffering from spasticity, multiple sclerosis, or amyotrophic lateral sclerosis, wherein said method comprises administering a dosage form comprising 6-20 mg of tizanidine wherein said tizanidine is released in manner such that tizanidine plasma drug concentration substantially ascends over a period of 10 hours following administration and where the peak plasma blood concentration of tizanidine is between 1.6-3.2 ng/ml.

In one embodiment, a pharmaceutical composition comprises a first layer of tizanidine and a second layer of tizanidine wherein said first layer is substantially released within 3 hours of administration and said second layer of tizanidine is substantially released over a period of 1-14 hours. In another embodiment, a pharmaceutical composition comprises a first layer of tizanidine and a second layer of tizanidine wherein said first layer is substantially released within 2 hours of administration and said second layer of tizanidine is substantially released over a period of 1-14 hours. In another embodiment, a pharmaceutical composition comprises a first layer of tizanidine and a second layer of tizanidine wherein said first layer is substantially released within 3 hours of administration and said second layer of tizanidine is substantially released over a period of 1-12 hours. In another embodiment, a pharmaceutical composition comprises a first layer of tizanidine and a second layer of tizanidine wherein said first layer is substantially released within 2 hours of administration and said second layer of tizanidine is substantially released over a period of 2-12 hours.

In another embodiment, a pharmaceutical composition comprises a first layer of tizanidine and a second layer of tizanidine wherein said first layer is substantially released within 3 hours of administration and said second layer of tizanidine is substantially released over a period of 1-12 hours and wherein wherein said first layer of tizanidine comprises between 5 and 25% of the tizanidine in said pharmaceutical composition. In another embodiment, a pharmaceutical composition comprises a first layer of tizanidine and a second layer of tizanidine wherein said first layer is substantially released within 3 hours of administration and said second layer of tizanidine is substantially released over a period of 1-12 hours and wherein wherein said first layer of tizanidine comprises between 10 and 15% of the tizanidine in said pharmaceutical composition. In another embodiment, a pharmaceutical composition comprises a first layer of tizanidine and a second layer of tizanidine wherein said first layer is substantially released within 3 hours of administration and said second layer of tizanidine is substantially released over a period of 1-12 hours and wherein wherein said first layer of tizanidine comprises about 12% of the tizanidine in said pharmaceutical composition. In another embodiment, a pharmaceutical composition comprises a first layer of tizanidine and a second layer of tizanidine wherein said first layer is substantially released within 3 hours of administration and said second layer of tizanidine is substantially released over a period of 1-12 hours and wherein said second layer of tizanidine comprises between 75 and 95% of the tizanidine in said pharmaceutical composition. In another embodiment, a pharmaceutical composition comprises a first layer of tizanidine and a second layer of tizanidine wherein said first layer is substantially released within 3 hours of administration and said second layer of tizanidine is substantially released over a period of 1-12 hours and wherein said second layer of tizanidine comprises between 85 and 95% of the tizanidine in said pharmaceutical composition. In another embodiment, a pharmaceutical composition comprises a first layer of tizanidine and a second layer of tizanidine wherein said first layer is substantially released within 3 hours of administration and said second layer of tizanidine is substantially released over a period of 1-12 hours and wherein said second layer of tizanidine comprises about 88% of the tizanidine in said pharmaceutical composition.

In another embodiment, a pharmaceutical composition comprises a first layer of tizanidine and a second layer of tizanidine wherein said first layer is substantially released within 3 hours of administration and said second layer of tizanidine is substantially released over a period of 1-12 hours and wherein said pharmaceutical composition is in the form of an osmotic drug delivery system.

In another embodiment, a pharmaceutical composition comprises a first layer of tizanidine of tizanidine and a second layer of tizanidine of tizanidine wherein said administration of said pharmaceutical composition results in patient peak plasma blood levels of between 1-4 ng/ml between 3-12 hours after administration. In a further embodiment, a pharmaceutical composition comprises a first layer of tizanidine of tizanidine and a second layer of tizanidine of tizanidine wherein said administration of said pharmaceutical composition results in patient peak plasma blood levels of between 1.6-3.2 ng/ml between 3-12 hours after administration.

In another embodiment, a pharmaceutical composition comprises a first layer of tizanidine and a second layer of tizanidine wherein said pharmaceutical composition contains between 6-20 mg of tizanidine. In a further embodiment, a pharmaceutical composition comprises a first layer of tizanidine and a second layer of tizanidine wherein said pharmaceutical composition contains between 14-18 mg of tizanidine. In a still further embodiment, a pharmaceutical composition comprises a first layer of tizanidine and a second layer of tizanidine wherein said pharmaceutical composition contains about 16 mg of tizanidine.

In another embodiment, the invention comprises a method of treating a condition which is responsive to tizanidine, the method comprising orally administering a tizanidine dosage form that produces a substantially increasing plasma tizanidine concentration following dosage administration.

In one embodiment, tizanidine is in the form of a salt. In another embodiment, tizanidine is in the form of a salt selected from acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. In a still further embodiment, tizanidine is in the form of tizanidine hemisuccinate sesquihydrate. In another embodiment, tizanidine is a polymorph, hydrate, co-crystal, or solvate.

In one embodiment, compositions of this invention have less side effects than immediate release tizanidine tablets or capsules. In another embodiment, compositions of this invention have less dry mouth than immediate release tizanidine tablets or capsules. In another embodiment, compositions of this invention have less somnolence than immediate release tizanidine tablets or capsules. In another embodiment, compositions of this invention have less sedation than immediate release tizanidine tablets or capsules. In another embodiment, compositions of this invention have less dizziness than immediate release tizanidine tablets or capsules.

In various embodiments, the controlled release dosage forms are formulated into dosage forms administrable to patients in need thereof. Controlled release dosage forms and methods of treatment using the controlled release dosage forms will now be described. It will be appreciated that the controlled release dosage forms described below are merely exemplary.

A variety of controlled release dosage forms are suitable for use in the present invention. In certain embodiments, the dosage form is orally administrable and is sized and shaped as a conventional tablet or capsule. Orally administrable dosage forms may be manufactured according to one of various different approaches. For example, the dosage form may be manufactured as a diffusion system, such as a reservoir device or matrix device, a dissolution system, such as encapsulated dissolution systems (including, for example, "tiny time pills", and beads) and matrix dissolution systems, and combination diffusion/dissolution systems and ion-exchange resin systems, as described in Pharmaceutical Sciences, Remington, 18$^{th}$ Ed., pp. 1676-1686 (1990), Mack Publishing Co.; The Pharmaceutical and Clinical Pharmacokinetics, 3$^{rd}$ Ed., pp. 1-28 (1984), Lea and Febreger, Pa.

Osmotic dosage forms in general utilize osmotic pressure to generate a driving force for imbibing fluid into a compartment formed, at least in part, by a semipermeable membrane that permits free diffusion of fluid but not drug or osmotic agent(s), if present. A significant advantage to osmotic systems is that operation is pH-independent and thus continues at the osmotically determined rate throughout an extended time period even as the dosage form transits the gastrointestinal tract and encounters differing microenvironments having significantly different pH values. A review of such dosage forms is found in Santus and Baker, "Osmotic drug delivery: a review of the patent literature," Journal of Controlled Release 35 (1995) 1-21. U.S. Pat. Nos. 3,845,770; 3,916,899; 3,995,631; 4,008,719; 4,111,202; 4,160,020; 4,327,725; 4,578,075; 4,681,583; 5,019,397; and 5,156,850 disclose osmotic devices for the continuous dispensing of active agent.

Osmotic dosage forms in which a drug composition is delivered as a slurry, suspension or solution from a small exit orifice by the action of an expandable layer are disclosed in U.S. Pat. Nos. 5,633,011; 5,190,765; 5,252,338; 5,620,705; 4,931,285; 5,006,346; 5,024,842; and 5,160,743, which are incorporated herein by reference. Typical devices include an expandable push layer and a drug layer surrounded by a semipermeable membrane. In certain instances, the drug layer is provided with a subcoat to delay release of the drug composition to the environment of use or to form an annealed coating in conjunction with the semipermeable membrane.

An exemplary dosage form, referred to in the art as an elementary osmotic pump dosage form, is shown in FIG. 1. Dosage form 20, shown in a cutaway view, is also referred to as an elementary osmotic pump, and is comprised of a semipermeable wall 22 that surrounds and encloses an internal compartment 24. The internal compartment contains a single component layer referred to herein as a drug layer 26, comprising an substance 28 in an admixture with selected excipients. The excipients are adapted to provide an osmotic activity gradient for attracting fluid from an external environment through wall 22 and for forming a deliverable complex formulation upon imbibition of fluid. The excipients may include a suitable suspending agent, also referred to herein as drug carrier 30, a binder 32, a lubricant 34, and an osmotically active agent referred to as an osmagent 36. Exemplary materials useful for these components can be found disclosed throughout the present application.

Semi-permeable wall 22 of the osmotic dosage form is permeable to the passage of an external fluid, such as water and biological fluids, but is substantially impermeable to the passage of components in the internal compartment. Materials useful for forming the wall are essentially nonerodible and are substantially insoluble in biological fluids during the life of the dosage form. Representative polymers for forming the semi-permeable wall include homopolymers and copolymers, such as, cellulose esters, cellulose ethers, and cellulose ester-ethers. Flux-regulating agents can be admixed with the wall-forming material to modulate the fluid permeability of the wall. For example, agents that produce a marked increase in permeability to fluid such as water are often essentially hydrophilic, while those that produce a marked permeability decrease to water are essentially hydrophobic. Exemplary flux regulating agents include polyhydric alcohols, polyalkylene glycols, polyalkylenediols, polyesters of alkylene glycols, and the like.

In operation, the osmotic gradient across wall 22 due to the presence of osmotically-active agents causes gastric fluid to be imbibed through the wall, swelling of the drug layer, and formation of a deliverable complex formulation (e.g., a solution, suspension, slurry or other flowable composition) within the internal compartment. The deliverable inventive substance formulation is released through an exit 38 as fluid continues to enter the internal compartment. Even as drug formulation is released from the dosage form, fluid continues to be drawn into the internal compartment, thereby driving continued release. In this manner, the substance is released in a controlled and continuous manner over an extended time period.

Wall 20 is formed to be permeable to the passage of an external fluid, such as water and biological fluids, and is substantially impermeable to the passage of paliperidone, osmagent, osmopolymer and the like. As such, it is semipermeable. The selectively semipermeable compositions used for forming wall 20 are essentially nonerodible and substantially insoluble in biological fluids during the life of the dosage form.

Representative polymers for forming wall 20 comprise semipermeable homopolymers, semipermeable copolymers, and the like. In one presently preferred embodiment, the compositions can comprise cellulose esters, cellulose ethers, and cellulose ester-ethers. The cellulosic polymers typically have a degree of substitution, "D.S.", on their anhydroglucose unit from greater than 0 up to 3 inclusive. By degree of substitution is meant the average number of hydroxyl groups originally present on the anhydroglucose unit that are replaced by a substituting group, or converted into another group. The anhydroglucose unit can be partially or completely substituted with groups such as acyl, alkanoyl, alkenoyl, aroyl, alkyl, alkoxy, halogen, carboalkyl, alkylcarbamate, alkylcarbonate, alkylsulfonate, alkylsulfamate, semipermeable polymer forming groups, and the like. The semipermeable compositions typically include a member selected from the group consisting of cellulose acylate, cellulose diacylate, cellulose triacylate, cellulose triacetate, cellulose acetate, cellulose diacetate, cellulose triacetate, mono-, di- and tri-cellulose alkanylates, mono-, di-, and tri-alkenylates, mono-, di-, and tri-aroylates, and the like.

Exemplary polymers can include, for example, cellulose acetate have a D.S. of 1.8 to 2.3 and an acetyl content of 32 to 39.9%; cellulose diacetate having a D.S. of 1 to 2 and an acetyl content of 21 to 35%, cellulose triacetate having a D.S. of 2 to 3 and an acetyl content of 34 to 44.8%, and the like. More specific cellulosic polymers include cellulose propionate having a D.S. of 1.8 and a propionyl content of 38.5%; cellulose acetate propionate having an acetyl content of 1.5 to 7% and an acetyl content of 39 to 42%; cellulose acetate propionate having an acetyl content of 2.5 to 3%, an average propionyl content of 39.2 to 45%, and a hydroxyl content of 2.8 to 5.4%; cellulose acetate butyrate having a D.S. of 1.8, an acetyl content of 13 to 15%, and a butyryl content of 34 to 39%; cellulose acetate butyrate having an acetyl content of 2 to 29%, a butyryl content of 17 to 53%, and a hydroxyl content of 0.5 to 4.7%; cellulose triacylates having a D.S. of 2.6 to 3 such as cellulose trivalerate, cellulose trilamate, cellulose tripalmitate, cellulose trioctanoate, and cellulose tripropionate; cellulose diesters having a D.S. of 2.2 to 2.6 such as cellulose disuccinate, cellulose dipalmitate, cellulose dioctanoate, cellulose dicarpylate, and the like; mixed cellulose esters such as cellulose acetate valerate, cellulose acetate succinate, cellulose propionate succinate, cellulose acetate octanoate, cellulose valerate palmitate, cellulose acetate heptonate, and the like. Semipermeable polymers are known in U.S. Pat. No. 4,077,407 and they can be synthesized by procedures described in Encyclopedia of Polymer Science and Technology, Vol. 3, pages 325 to 354, 1964, published by Interscience Publishers, Inc., New York.

Additional semipermeable polymers for forming the semipermeable wall can comprise, for example, cellulose acetaldehyde dimethyl acetate; cellulose acetate ethylcarbamate; cellulose acetate methylcarbamate; cellulose dimethylaminoacetate; semipermeable polyamide; semipermeable polyurethanes; semipermeable sulfonated polystyrenes; crosslinked selectively semipermeable polymers formed by the coprecipitation of a polyanion and a polycation as disclosed in U.S. Pat. Nos. 3,173,876; 3,276,586; 3,541,005; 3,541,006; and 3,546,142; semipermeable polymers as disclosed in U.S. Pat. No. 3,133,132; semipermeable polystyrene derivatives; semipermeable poly(sodium styrenesulfonate); semipermeable poly(vinylbenzyltremethylammonium chloride); semipermeable polymers, exhibiting a fluid permeability of $10^{-5}$ to $10^{-2}$ (cc. mil/cm hr.atm) expressed as per atmosphere of hydrostatic or osmotic pressure differences across a semipermeable wall. The polymers are known to the art in U.S. Pat. Nos. 3,845,770; 3,916,899; and 4,160,020; and in Handbook of Common Polymers, by Scott, J. R., and Roff, W. J., 1971, published by CRC Press, Cleveland. Ohio.

Wall 20 may also comprise a flux-regulating agent. The flux regulating agent is a compound added to assist in regulating the fluid permeability or flux through the wall 20. The flux regulating agent can be a flux enhancing agent or a decreasing agent. The agent can be preselected to increase or decrease the liquid flux. Agents that produce a marked increase in permeability to fluids such as water are often essentially hydrophilic, while those that produce a marked decrease to fluids such as water are essentially hydrophobic. The amount of regulator in wall 20 when incorporated therein generally is from about 0.01% to 20% by weight or more. The flux regulator agents in one embodiment that increase flux include, for example, polyhydric alcohols, polyalkylene glycols, polyalkylenediols, polyesters of alkylene glycols, and the like. Typical flux enhancers include polyethylene glycol 300, 400, 600, 1500, 4000, 6000, poly(ethylene glycol-co-propylene glycol), and the like; low molecular weight gylcols such as polypropylene glycol, polybutylene glycol and polyamylene glycol: the polyalkylenediols such as poly(1,3-propanediol), poly(1,4-butanediol), poly(1,6-hexanediol), and the like; aliphatic diols such as 1,3-butylene glycol, 1,4-pentamethylene glycol, 1,4-hexamethylene glycol, and the like; alkylene triols such as glycerine, 1,2,3-butanetriol, 1,2,4-hexanetriol, 1,3,6-hexanetriol and the like; esters such as ethylene glycol dipropionate, ethylene glycol butyrate, butylene glucol dipropionate, glycerol acetate esters, and the like. Representative flux decreasing agents include, for example, phthalates substituted with an alkyl or alkoxy or with both an alkyl and alkoxy group such as diethyl phthalate, dimethoxyethyl phthalate, dimethyl phthalate, and [di(2-ethylhexyl)phthalate], aryl phthalates such as triphenyl phthalate, and butyl benzyl phthalate; insoluble salts such as calcium sulphate, barium sulphate, calcium phosphate, and the like; insoluble oxides such as titanium oxide; polymers in powder, granule and like form such as polystyrene, polymethylmethacrylate, polycarbonate, and polysulfone; esters such as citric acid esters esterfied with long chain alkyl groups; inert and substantially water impermeable fillers; resins compatible with cellulose based wall forming materials, and the like.

Other materials that can be used to form wall 20 for imparting flexibility and elongation properties to the wall, for making the wall less-to-nonbrittle and to render tear strength, include, for example, phthalate plasticizers such as dibenzyl phthalate, dihexyl phthalate, butyl octyl phthalate, straight chain phthalates of six to eleven carbons, di-isononyl phthalte, di-isodecyl phthalate, and the like. The plasticizers include nonphthalates such as triacetin, dioctyl azelate, epoxidized tallate, tri-isoctyl trimellitate, tri-isononyl trimellitate, sucrose acetate isobutyrate, epoxidized soybean oil, and the like. The amount of plasticizer in a wall when incorporated therein is about 0.01% to 20% weight, or higher.

Figure 2:
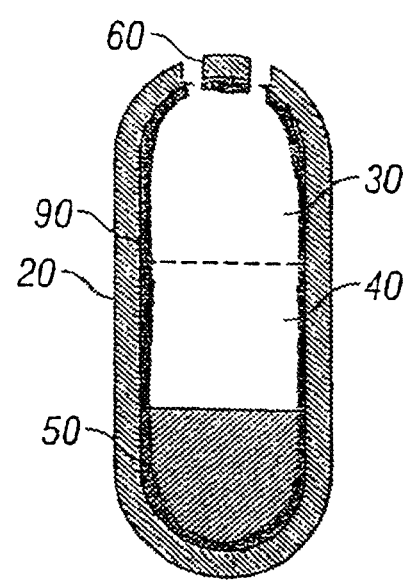
FIG. 2: An exemplary osmotic delivery device.

FIG. 2 shows an embodiment of one type of controlled release dosage form, namely the osmotic controlled release dosage form. First drug layer 30 comprises osmotically active components, and a lower amount of active agent than in second drug layer 40. The osmotically active component(s) in the first component drug layer comprises an osmagent such as salt and one or more osmopolymer(s) having relatively small molecular weights which exhibit swelling as fluid is imbibed such that release of these osmopolymers through exit 60 occurs similar to that of drug layer 40. Additional excipients such as binders, lubricants, antioxidants and colorants may also be included in first drug layer 30.

Second drug layer 40 comprises active agent in an admixture with selected excipients adapted to provide an osmotic activity gradient for driving fluid from an external environment through membrane 20 and for forming a deliverable drug formulation upon imbibition of fluid. The excipients may include a suitable suspending agent, also referred to herein as a drug carrier, but no osmotically active agent, "osmagent," such as salt, sodium chloride. It has been discovered that the omission of salt from this second drug layer, which contains a higher proportion of the overall drug in the dosage form, in combination with the salt in the first drug layer, provides an improved ascending rate of release creating a longer duration of ascending rate.

Drug layer 40 has a higher concentration of the drug than does drug layer 30. The ratio of the concentration of drug in the first drug layer 30 to the concentration of drug in the second drug layer 40 is maintained at less than 1 and preferably less than or equal to about 0.43 to provide the desired substantially ascending rate of release. Drug layer 40 may also comprise other excipients such as lubricants, binders, etc. Drug layer 40, as with drug layer 30, further comprises a hydrophilic polymer carrier. The hydrophilic polymer provides a particle in the drug composition that contributes to the controlled delivery of the active drug. Representative examples of these polymers are poly(alkylene oxide) of 100,000 to 750,000 number-average molecular weight, including poly(ethylene oxide), poly(methylene oxide), poly(butylene oxide) and poly(hexylene oxide); and a poly(carboxymethylcellulose) of 40,000 to 400,000 number-average molecular weight, represented by poly(alkali carboxymethylcellulose), poly(sodium carboxymethylcellulose), poly(potassium carboxymethylcellulose) and poly(lithium carboxymethylcellulose). Drug layer 40 can further comprise a hydroxypropylalkylcellulose of 9,200 to 125,000 number-average molecular weight for enhancing the delivery properties of the dosage form as represented by hydroxypropylethylcellulo- se, hydroxypropylmethylcellulose, hydroxypropylbutylcellulose and hydroxypropylpentylcellulose; and a poly(vinylpyrrolidone) of 7,000 to 75,000 number-average molecular weight for enhancing the flow properties of the dosage form. Preferred among these polymers are the poly(ethylene oxide) of 100,000-300,000 number average molecular weight. Carriers that erode in the gastric environment, i.e., bioerodible carriers, are especially preferred.

Other carriers that may be incorporated into drug layer 40, and/or drug layer 30, include carbohydrates that exhibit sufficient osmotic activity to be used alone or with other osmagents. Such carbohydrates comprise monosaccharides, disaccharides and polysaccharides. Representative examples include maltodextrins (i.e., glucose polymers produced by the hydrolysis of corn starch) and the sugars comprising lactose, glucose, raffinose, sucrose, mannitol, sorbitol, and the like. Preferred maltodextrins are those having a dextrose equivalence (DE) of 20 or less, preferably with a DE ranging from about 4 to about 20, and often 9-20. Maltodextrin having a DE of 9-12 has been found to be useful. Drug layer 40 and drug layer 30 typically will be a substantially dry, <1% water by weight, composition formed by compression of the carrier, the drug, and other excipients as one layer.

Drug layer 40 may be formed from particles by comminution that produces the size of the drug and the size of the accompanying polymer used in the fabrication of the drug layer, typically as a core containing the compound, according to the mode and the manner of the invention. The means for producing particles include granulation, spray drying, sieving, lyophilization, crushing, grinding, jet milling, micronizing and chopping to produce the intended micron particle size. The process can be performed by size reduction equipment, such as a micropulverizer mill, a fluid energy grinding mill, a grinding mill, a roller mill, a hammer mill, an attrition mill, a chaser mill, a ball mill, a vibrating ball mill, an impact pulverizer mill, a centrifugal pulverizer, a coarse crusher and a fine crusher. The size of the particle can be ascertained by screening, including a grizzly screen, a flat screen, a vibrating screen, a revolving screen, a shaking screen, an oscillating screen and a reciprocating screen. The processes and equipment for preparing drug and carrier particles are disclosed in Pharmaceutical Sciences, Remington, $17^{th}$ Ed., pp. 1585-1594 (1985); Chemical Engineers Handbook, Perry, $6^{th}$ Ed., pp. 21-13 to 21-19 (1984); Journal of Pharmaceutical Sciences, Parrot, Vol. 61, No. 6, pp. 813-829 (1974); and Chemical Engineer, Hixon, pp. 94-103 (1990).

First drug layer 30 comprises active agent in an admixture with selected excipients adapted to provide an osmotic activity gradient for driving fluid from an external environment through membrane 20 and for forming a deliverable drug formulation upon imbibition of fluid. The excipients may include a suitable suspending agent, also referred to herein as a drug carrier, and an osmotically active agent, i.e., an "osmagent," such as salt. Other excipients such as lubricants, binders, etc. may also be included. It has been surprisingly found that when first component drug layer 30 comprises an osmotically active component, and a lower amount of active drug than in second component drug layer 40, an improved ascending rate of release can be created that provides a longer duration of ascending rate. Additionally, with the low doses of paliperidone delivered from a dosage form, and the low amount of that total in the first drug layer 30, the addition of salt has been found to provide a consistent predetermined release rate providing a substantially ascending rate of release over 20 hours.

The osmotically active component in the first drug layer typically comprises an osmagent and one or more osmopolymer(s) having relatively small molecular weights which exhibit swelling as fluid is imbibed such that release of these osmopolymers through exit 60 occurs similar to that of drug layer 40.

The ratio of drug concentration between the first drug layer and the second drug layer alters the release rate profile. Release rate profile is calculated as the difference between the maximum release rate and the release rate achieved at the first time point after start-up (for example, at 6 hours), divided by the average release rate between the two data points.

Drug layer 30 and drug layer 40 may optionally contain surfactants and disintegrants in both drug layers. Exemplary of the surfactants are those having an HLB value of about 10-25, such as polyethylene glycol 400 monostearate, polyoxyethylene-4-sorbitan monolaurate, polyoxyethylene-20-sorbitan monooleate, polyoxyethylene-20-sorbitan monopalmitate, polyoxyethylene-20-monolaurate, polyoxyethylene-40-stearat-e, sodium oleate and the like.

Disintegrants may be selected from starches, clays, celluloses, algins and gums and crosslinked starches, celluloses and polymers. Representative disintegrants include corn starch, potato starch, croscarmelose, crospovidone, sodium starch glycolate, Veegum HV, methylcellulose, agar, bentonite, carboxymethylcellulose, alginic acid, guar gum and the like.

The expandable layer comprises in one embodiment a hydroactivated composition that swells in the presence of water, such as that present in gastric fluids. Conveniently, it can comprise an osmotic composition comprising an osmotic solute that exhibits an osmotic pressure gradient across the semipermeable layer against an external fluid present in the environment of use. In another embodiment, the hydro-activated layer comprises a hydrogel that imbibes and/or absorbs fluid into the layer through the outer semipermeable wall. The semipermeable wall is non-toxic. It maintains its physical and chemical integrity during operation and it is essentially free of interaction with the expandable layer.

The expandable layer in one preferred embodiment comprises a hydroactive layer comprising a hydrophilic polymer, also known as osmopolymers. The osmopolymers exhibit fluid imbibition properties. The osmopolymers are swellable, hydrophilic polymers, which osmopolymers interact with water and biological aqueous fluids and swell or expand to an equilibrium state. The osmopolymers exhibit the ability to swell in water and biological fluids and retain a significant portion of the imbibed fluid within the polymer structure. The osmopolymers swell or expand to a very high degree, usually exhibiting a 2 to 50 fold volume increase. The osmopolymers can be non-cross-linked or cross-linked. The swellable, hydrophilic polymers are in one embodiment lightly cross-linked, such cross-links being formed by covalent or ionic bonds or residue crystalline regions after swelling. The osmopolymers can be of plant, animal or synthetic origin.

The osmopolymers are hydrophilic polymers. Hydrophilic polymers suitable for the present purpose include poly(hydroxy-alkyl methacrylate) having a molecular weight of from 30,000 to 5,000,000; poly(vinylpyrrolidone) having a molecular weight of from 10,000 to 360,000; anionic and cationic hydrogels; polyelectrolytes complexes; poly(vinyl alcohol) having a low acetate residual, cross-linked with glyoxal, formaldehyde, or glutaraldehyde and having a degree of polymerization of from 200 to 30,000; a mixture of methyl cellulose, cross-linked agar and carboxymethyl cellulose; a mixture of hydroxypropyl methylcellulose and sodium carboxymethylcellulose; a mixture of hydroxypropyl ethylcellulose and sodium carboxymethyl cellulose, a mixture of sodium carboxymethylcellulose and methylcellulose, sodium carboxymethylcellulose; potassium carboxymethylcellulose; a water insoluble, water swellable copolymer formed from a dispersion of finely divided copolymer of maleic anhydride with styrene, ethylene, propylene, butylene or isobutylene crosslinked with from 0.001 to about 0.5 moles of saturated cross-linking agent per mole of maleic anhydride per copolymer; water swellable polymers of N-vinyl lactams; polyoxyethylene-polyoxypropy-lene gel; carob gum; polyacrylic gel; polyester gel; polyuria gel; polyether gel, polyamide gel; polycellulosic gel; polygum gel; initially dry hydrogels that imbibe and absorb water which penetrates the glassy hydrogel and lowers its glass temperature; and the like.

Representative of other osmopolymers are polymers that form hydrogels such as Carbopol.™ acidic carboxypolymer, a polymer of acrylic acid cross-linked with a polyallyl sucrose, also known as carboxypolymethylene, and carboxyvinyl polymer having a molecular weight of 250,000 to 4,000,000; Cyanamer.™. polyacrylamides; cross-linked water swellable indenemaleic anhydride polymers; Goodrite.™. polyacrylic acid having a molecular weight of 80,000 to 200,000; Polyox.™. polyethylene oxide polymer having a molecular weight of 100,000 to 5,000,000 and higher; starch graft copolymers; Aqua-Keeps.™. acrylate polymer polysaccharides composed of condensed glucose units such as diester cross-linked polygluran; and the like. Representative polymers that form hydrogels are known to the prior art in U.S. Pat. No. 3,865,108; U.S. Pat. No. 4,002,173; U.S. Pat. No. 4,207,893; and in Handbook of Common Polymers, by Scott and Roff, published by the Chemical Rubber Co., Cleveland, Ohio. The amount of osmopolymer comprising a hydro-activated layer can be from about 5% to 100%.

The expandable layer in another manufacture can comprise an osmotically effective compound that comprises inorganic and organic compounds that exhibit an osmotic pressure gradient across a semipermeable wall against an external fluid. The osmotically effective compounds, as with the osmopolymers, imbibe fluid into the osmotic system, thereby making available fluid to push against the inner wall, i.e., in some embodiments, the barrier layer and/or the wall of the soft or hard capsule for pushing active agent from the dosage form. The osmotically effective compounds are known also as osmotically effective solutes, and also as osmagents. Osmotically effective solutes that can be used comprise magnesium sulfate, magnesium chloride, potassium sulfate, sodium sulfate, lithium sulfate, potassium acid phosphate, mannitol, urea, inositol, magnesium succinate, tartaric acid, carbohydrates such as raffinose, sucrose, glucose, lactose, sorbitol, and mixtures therefor. The amount of osmagent in can be from about 5% to 100% of the weight of the layer. The expandable layer optionally comprises an osmopolymer and an osmagent with the total amount of osmopolymer and osmagent equal to 100%. Osmotically effective solutes are known to the prior art as described in U.S. Pat. No. 4,783,337.

Pan coating may be conveniently used to provide the completed dosage form, except for the exit orifice. In the pan coating system, the wall-forming composition for the inner wall or the outer wall, as the case may be, is deposited by successive spraying of the appropriate wall composition onto the compressed trilayered or multilayered core comprising the drug layers, optional barrier layer and push layer, accompanied by tumbling in a rotating pan. A pan coater is used because of its availability at commercial scale. Other techniques can be used for coating the compressed core. Once coated, the wall is dried in a forced-air oven or in a temperature and humidity controlled oven to free the dosage form of solvent(s) used in the manufacturing. Drying conditions will be conventionally chosen on the basis of available equipment, ambient conditions, solvents, coatings, coating thickness, and the like.

Other coating techniques can also be employed. For example, the wall or walls of the dosage form may be formed in one technique using the air-suspension procedure. This procedure consists of suspending and tumbling the compressed core in a current of air and the semipermeable wall forming composition, until the wall is applied to the core. The air-suspension procedure is well suited for independently forming the wall of the dosage form. The air-suspension procedure is described in U.S. Pat. No. 2,799,241; in J. Am. Pharm. Assoc., Vol. 48, pp. 451-459 (1959); and, ibid., Vol. 49, pp. 82-84 (1960). The dosage form also can be coated with a Wurster.™. air-suspension coater using, for example, methylene dichloride methanol as a cosolvent for the wall forming material. An Aeromatic.™. air-suspension coater can be used employing a cosolvent.

In an embodiment, the controlled release dosage form of the invention is provided with at least one exit 60 as shown in FIG. 2. Exit 60 cooperates with the compressed core for the uniform release of drug from the dosage form. The exit can be provided during the manufacture of the dosage form or during drug delivery by the dosage form in a fluid environment of use.

One or more exit orifices are drilled in the drug layer end of the dosage form, and optional water soluble overcoats, which may be colored (e.g., Opadry colored coatings) or clear (e.g., Opadry Clear), may be coated on the dosage form to provide the finished dosage form.

An exit, or a plurality of exits, can be formed by leaching a member selected from the group consisting of sorbitol, lactose, fructose, glucose, mannose, galactose, talose, sodium chloride, potassium chloride, sodium citrate and mannitol to provide a uniform-release dimensioned pore-exit orifice. The exit can have any shape, such as round, triangular, square, elliptical and the like for the uniform metered dose release of a drug from the dosage form. The controlled release dosage form can be constructed with one or more exits in spaced-apart relation or one or more surfaces of the controlled release dosage form. Drilling, including mechanical and laser drilling, through the semipermeable wall can be used to form the exit orifice. Such exits and equipment for forming such exits are disclosed in U.S. Pat. No. 3,916,899, by Theeuwes and Higuchi and in U.S. Pat. No. 4,088,864, by Theeuwes, et al.

Dosage forms in accordance with the embodiments depicted in FIG. 1 are manufactured by standard techniques.

For example, the dosage form may be manufactured by the wet granulation technique. In the wet granulation technique, the drug and carrier are blended using an organic solvent, such as denatured anhydrous ethanol, as the granulation fluid. The remaining ingredients can be dissolved in a portion of the granulation fluid, such as the solvent described above, and this latter prepared wet blend is slowly added to the drug blend with continual mixing in the blender. The granulating fluid is added until a wet blend is produced, which wet mass blend is then forced through a predetermined screen onto oven trays. The blend is dried for 18 to 24 hours at 24.degree. C. to 35.degree. C. in a forced-air oven. The dried granules are then sized. Next, magnesium stearate, or another suitable lubricant, is added to the drug granulation, and the granulation is put into milling jars and mixed on a jar mill for 10 minutes. The composition is pressed into a layer, for example, in a Manesty.™. press or a Korsch LCT press. For a trilayered core, granules or powders of the drug layer compositions and push layer composition are sequentially placed in an appropriately-sized die with intermediate compression steps being applied to each of the first two layers, followed by a final compression step after the last layer is added to the die to form the trilayered core. The intermediate compression typically takes place under a force of about 50-100 newtons. Final stage compression typically takes place at a force of 3500 newtons or greater, often 3500-5000 newtons. The compressed cores are fed to a dry coater press, e.g., Kilian.™. Dry Coater press, and subsequently coated with the wall materials as described above.

In another embodiment, the drug and other ingredients comprising the drug layer are blended and pressed into a solid layer. The layer possesses dimensions that correspond to the internal dimensions of the area the layer is to occupy in the dosage form, and it also possesses dimensions corresponding to the push layer, if included, for forming a contacting arrangement therewith. The drug and other ingredients can also be blended with a solvent and mixed into a solid or semisolid form by conventional methods, such as ballmilling, calendering, stirring or rollmilling, and then pressed into a preselected shape. Next, if included, a layer of osmopolymer composition is placed in contact with the layer of drug in a like manner. The layering of the drug formulation and the osmopolymer layer can be fabricated by conventional two-layer press techniques. An analogous procedure may be followed for the preparation of the trilayered core. The compressed cores then may be coated with the inner wall material and the semipermeable wall material as described above.

The osmotic dosage forms of the present invention can possess two distinct forms, a soft capsule form and a hard capsule form. The soft capsule, as used by the present invention, preferably in its final form comprises one piece. The one-piece capsule is of a sealed construction encapsulating the drug formulation therein. The capsule can be made by various processes including the plate process, the rotary die process, the reciprocating die process, and the continuous process. An example of the plate process is as follows. The plate process uses a set of molds. A warm sheet of a prepared capsule lamina-forming material is laid over the lower mold and the formulation poured on it. A second sheet of the lamina-forming material is placed over the formulation followed by the top mold. The mold set is placed under a press and a pressure applied, with or without heat, to form a unit capsule. The capsules are washed with a solvent for removing excess agent formulation from the exterior of the capsule, and the air-dried capsule is encapsulated with a semipermeable wall. The rotary die process uses two continuous films of capsule lamina-forming material that are brought into convergence between a pair of revolving dies and an injector wedge. The process fills and seals the capsule in dual and coincident operations. In this process, the sheets of capsule lamina-forming material are fed over guide rolls, and then down between the wedge injector and the die rolls. The agent formulation to be encapsulated flows by gravity into a positive displacement pump. The pump meters the agent formulation through the wedge injector and into the sheets between the die rolls. The bottom of the wedge contains small orifices lined up with the die pockets of the die rolls. The capsule is about half-sealed when the pressure of pumped agent formulation forces the sheets into the die pockets, wherein the capsules are simultaneously filled, shaped, hermetically sealed and cut from the sheets of lamina-forming materials. The sealing of the capsule is achieved by mechanical pressure on the die rolls and by heating of the sheets of lamina-forming materials by the wedge. After manufacture, the agent formulation-filled capsules are dried in the presence of forced air, and a semipermeable lamina encapsulated thereto.

The reciprocating die process produces capsules by leading two films of capsule lamina-forming material between a set of vertical dies. The dies as they close, open, and close perform as a continuous vertical plate forming row after row of pockets across the film. The pockets are filled with an inventive formulation, and as the pockets move through the dies, they are sealed, shaped, and cut from the moving film as capsules filled with agent formulation. A semipermeable encapsulating lamina is coated thereon to yield the capsule. The continuous process is a manufacturing system that also uses rotary dies, with the added feature that the process can successfully fill active agent in dry powder form into a soft capsule, in addition to encapsulating liquids. The filled capsule of the continuous process is encapsulated with a semipermeable polymeric material to yield the capsule. Procedures for manufacturing soft capsules are disclosed in U.S. Pat. No. 4,627,850 and U.S. Pat. No. 6,419,952.

The dosage forms of the present invention can also be made from an injection-moldable composition by an injection-molding technique. Injection-moldable compositions provided for injection-molding into the semipermeable wall comprise a thermoplastic polymer, or the compositions comprise a mixture of thermoplastic polymers and optional injection-molding ingredients. The thermoplastic polymer that can be used for the present purpose comprise polymers that have a low softening point, for example, below 200.degree. C., preferably within the range of 40.degree. C. to 180.degree. C. The polymers, are preferably synthetic resins, addition polymerized resins, such as polyamides, resins obtained from diepoxides and primary alkanolamines, resins of glycerine and phthalic anhydrides, polymethane, polyvinyl resins, polymer resins with end-positions free or esterified carboxyl or caboxamide groups, for example with acrylic acid, acrylic amide, or acrylic acid esters, polycaprolactone, and its copolymers with dilactide, diglycolide, valerolactone and decalactone, a resin composition comprising polycaprolactone and polyalkylene oxide, and a resin composition comprising polycaprolactone, a polyalkylene oxide such as polyethylene oxide, poly(cellulose) such as poly(hydroxypropylmethylcellulose), poly(hydroxyethylmethylcellulose), and poly(hydroxypropylcellulose). The membrane forming composition can comprise optional membrane-forming ingredients such as polyethylene glycol, talcum, polyvinylalcohol, lactose, or polyvinyl pyrrolidone. The compositions for forming an injection-molding polymer composition can comprise 100% thermoplastic polymer. The composition in another embodiment comprises 10% to 99% of a thermoplastic polymer and 1% to 90% of a different polymer with the total equal to 100%. The invention provides also a thermoplastic polymer composition comprising 1% to 98% of a first thermoplastic polymer, 1% to 90% of a different, second polymer and 1% to 90% of a different, third polymer with all polymers equal to 100%. Representation composition comprises 20% to 90% of thermoplastic polycaprolactone and 10% to 80% of poly(alkylene oxide); a composition comprising 20% to 90% polycaprolactone and 10% to 60% of poly(ethylene oxide) with the ingredients equal to 100%; a composition comprising 10% to 97% of polycaprolactone, 10% to 97% poly(alkylene oxide), and 1% to 97% of poly(ethylene glycol) with all ingredients equal to 100%; a composition comprising 20% to 90% polycaprolactone and 10% to 80% of poly(hydroxypropylcellulose) with all ingredients equal to 100%; and a composition comprising 1% to 90% polycaprolactone, 1% to 90% poly(ethylene oxide), 1% to 90% poly(hydroxypropylcellulose) and 1% to 90% poly(ethylene glycol) with all ingredients equal to 100%. The percent expressed is weight percent wt %.

In another embodiment of the invention, a composition for injection-molding to provide a membrane can be prepared by blending a composition comprising a polycaprolactone 63 wt %, polyethylene oxide 27 wt %, and polyethylene glycol 10 wt % in a conventional mixing machine, such as a Moriyama.™. Mixer at 65.degree. C. to 95.degree. C., with the ingredients added to the mixer in the following addition sequence, polycaprolactone, polyethylene oxide and polyethylene glycol. In one example, all the ingredients are mixed for 135 minutes at a rotor speed of 10 to 20 rpm. Next, the blend is fed to a Baker Perkins Kneader.™. extruder at 80.degree. C. to 90.degree. C., at a pump speed of 10 rpm and a screw speed of 22 rpm, and then cooled to 10.degree. C. to 12.degree. C., to reach a uniform temperature. Then, the cooled extruded composition is fed to an Albe Pelletizer, converted into pellets at 250.degree. C., and a length of 5 mm. The pellets next are fed into an injection-molding machine, an Arburg Allrounder.™. at 200.degree. F. to 350.degree. C. (93.degree. C. to 177.degree. C.), heated to a molten polymeric composition, and the liquid polymer composition forced into a mold cavity at high pressure and speed until the mold is filled and the composition comprising the polymers are solidified into a preselected shape. The parameters for the injection-molding consists of a band temperature through zone 1 to zone 5 of the barrel of 195.degree. F. (91.degree. C.) to 375.degree. F., (191.degree. C.), an injection-molding pressure of 1818 bar, a speed of 55 cm3/s, and a mold temperature of 75.degree. C. The injection-molding compositions and injection-molding procedures are disclosed in U.S. Pat. No. 5,614,578.

Alternatively, the capsule can be made conveniently in two parts, with one part (the "cap") slipping over and capping the other part (the "body") as long as the capsule is deformable under the forces exerted by the expandable layer and seals to prevent leakage of the liquid, active agent formulation from between the telescoping portions of the body and cap. The two parts completely surround and capsulate the internal lumen that contains the liquid, active agent formulation, which can contain useful additives. The two parts can be fifted together after the body is filled with a preselected formulation. The assembly can be done by slipping or telescoping the cap section over the body section, and sealing the cap and body, thereby completely surrounding and encapsulating the formulation of active agent.

Soft capsules typically have a wall thickness that is greater than the wall thickness of hard capsules. For example, soft capsules can, for example, have a wall thickness on the order of 10-40 mils, about 20 mils being typical, whereas hard capsules can, for example, have a wall thickness on the order of 2-6 mils, about 4 mils being typical.

In one embodiment of the dosage system, a soft capsule can be of single unit construction and can be surrounded by an unsymmetrical hydro-activated layer as the expandable layer. The expandable layer will generally be unsymmetrical and have a thicker portion remote from the exit orifice. As the hydro-activated layer imbibes and/or absorbs external fluid, it expands and applies a push pressure against the wall of capsule and optional barrier layer and forces active agent formulation through the exit orifice. The presence of an unsymmetrical layer functions to assure that the maximum dose of agent is delivered from the dosage form, as the thicker section of layer distant from passageway swells and moves towards the orifice.

In yet another configuration, the expandable layer can be formed in discrete sections that do not entirely encompass an optionally barrier layer-coated capsule. The expandable layer can be a single element that is formed to fit the shape of the capsule at the area of contact. The expandable layer can be fabricated conveniently by tableting to form the concave surface that is complementary to the external surface of the barrier-coated capsule. Appropriate tooling such as a convex punch in a conventional tableting press can provide the necessary complementary shape for the expandable layer. In this case, the expandable layer is granulated and compressed, rather than formed as a coating. The methods of formation of an expandable layer by tableting are well known, having been described, for example in U.S. Pat. Nos. 4,915,949; 5,126,142; 5,660,861; 5,633,011; 5,190,765; 5,252,338; 5,620,705; 4,931,285; 5,006,346; 5,024,842; and 5,160,743.

In some embodiments, a barrier layer can be first coated onto the capsule and then the tableted, expandable layer is attached to the barrier-coated capsule with a biologically compatible adhesive. Suitable adhesives include, for example, starch paste, aqueous gelatin solution, aqueous gelatin/glycerin solution, acrylate-vinylacetate based adhesives such as Duro-Tak adhesives (National Starch and Chemical Company), aqueous solutions of water soluble hydrophilic polymers such as hydroxypropyl methyl cellulose, hydroxymethyl cellulose, hydroxyethyl cellulose, and the like. That intermediate dosage form can be then coated with a semipermeable layer. The exit orifice is formed in the side or end of the capsule opposite the expandable layer section. As the expandable layer imbibes fluid, it will swell. Since it is constrained by the semipermeable layer, as it expands it will compress the barrier-coated capsule and express the liquid, active agent formulation from the interior of the capsule into the environment of use.

The hard capsules are typically composed of two parts, a cap and a body, which are fitted together after the larger body is filled with a preselected appropriate formulation. This can be done by slipping or telescoping the cap section over the body section, thus completely surrounding and encapsulating the useful agent formulation. Hard capsules can be made, for example, by dipping stainless steel molds into a bath containing a solution of a capsule lamina-forming material to coat the mold with the material. Then, the molds are withdrawn, cooled, and dried in a current of air. The capsule is stripped from the mold and trimmed to yield a lamina member with an internal lumen. The engaging cap that telescopically caps the formulation receiving body is made in a similar manner. Then, the closed and filled capsule can be encapsulated with a semipermeable lamina. The semipermeable lamina can be applied to capsule parts before or after parts and are joined into the final capsule. In another embodiment, the hard capsules can be made with each part having matched locking rings near their opened end that permit joining and locking together the overlapping cap and body after filling with formulation. In this embodiment, a pair of matched locking rings are formed into the cap portion and the body portion, and these rings provide the locking means for securely holding together the capsule. The capsule can be manually filled with the formulation, or they can be machine filled with the formulation. In the final manufacture, the hard capsule is encapsulated with a semipermeable lamina permeable to the passage of fluid and substantially impermeable to the passage of useful agent. Methods of forming hard cap dosage forms are described in U.S. Pat. No. 6,174,547, U.S. Pat. Nos. 6,596, 314, 6,419,952, and 6,174,547.

The hard and soft capsules can comprise, for example, gelatin; gelatin having a viscosity of 15 to 30 millipoises and a bloom strength up to 150 grams; gelatin having a bloom value of 160 to 250; a composition comprising gelatin, glycerine, water and titanium dioxide; a composition comprising gelatin, erythrosin, iron oxide and titanium dioxide; a composition comprising gelatin, glycerine, sorbitol, potassium sorbate and titanium dioxide; a composition comprising gelatin, acacia glycerine, and water; and the like. Materials useful for forming capsule wall are known in U.S. Pat. No. 4,627, 850; and in U.S. Pat. No. 4,663,148. Alternatively, the capsules can be made out of materials other than gelatin (see for example, products made by BioProgres plc).

The capsules typically can be provided, for example, in sizes from about 3 to about 22 minims (1 minim being equal to 0.0616 ml) and in shapes of oval, oblong or others. They can be provided in standard shape and various standard sizes, conventionally designated as (000), (00), (0), (1), (2), (3), (4), and (5). The largest number corresponds to the smallest size. Non-standard shapes can be used as well. In either case of soft capsule or hard capsule, non-conventional shapes and sizes can be provided if required for a particular application.

The osmotic devices of the present invention may comprise a semipermeable wall permeable to the passage of exterior biological fluid and substantially impermeable to the passage of benzisoxazole derivative formulation. The selectively permeable compositions used for forming the wall are essentially non-erodible and they are insoluble in biological fluids during the life of the osmotic system. The semipermeable wall comprises a composition that does not adversely affect the host, the benzisoxazole derivative formulation, an osmopolymer, osmagent and the like. Materials useful in the formation of a semipermeable wall are disclosed elsewhere herein.

The semipermeable wall can also comprise a flux regulating agent. Materials useful flux regulating agents are disclosed elsewhere herein. Other materials that can be used to form the semipermeable wall for imparting flexibility and elongation properties to the semipermeable wall are also disclosed elsewhere herein.

The semipermeable wall surrounds and forms a compartment containing a one or a plurality of layers, one of which is an expandable layer which in some embodiments, can contain osmotic agents. The composition of such expandable layers is disclosed elsewhere herein.

In certain solid and liquid embodiments, the dosage forms further can comprise a barrier layer. The barrier layer in certain embodiments is deformable under the pressure exerted by the expandable layer and will be impermeable (or less permeable) to fluids and materials that can be present in the expandable layer, the liquid active agent formulation and in the environment of use, during delivery of the active agent formulation. A certain degree of permeability of the barrier layer can be permitted if the delivery rate of the active agent formulation is not detrimentally effected. However, it is preferred that barrier layer not completely transport through it fluids and materials in the dosage form and the environment of use during the period of delivery of the active agent. The barrier layer can be deformable under forces applied by expandable layer so as to permit compression of capsule to force the liquid, active agent formulation from the exit orifice. In some embodiments, the barrier layer will be deformable to such an extent that it create a seal between the expandable layer and the semipermeable layer in the area where the exit orifice is formed. In that manner, the barrier layer will deform or flow to a limited extent to seal the initially, exposed areas of the expandable layer and the semipermeable layer when the exit orifice is being formed, such as by drilling or the like, or during the initial stages of operation. When sealed, the only avenue for liquid permeation into the expandable layer is through the semipermeable layer, and there is no back-flow of fluid into the expandable layer through the exit orifice.

Suitable materials for forming the barrier layer can include, for example, polyethylene, polystyrene, ethylene-vinyl acetate copolymers, polycaprolactone and Hytrel.™. polyester elastomers (Du Pont), cellulose acetate, cellulose acetate pseudolatex (such as described in U.S. Pat. No. 5,024,842), cellulose acetate propionate, cellulose acetate butyrate, ethyl cellulose, ethyl cellulose pseudolatex (such as Surelease.™. as supplied by 10 Colorcon, West Point, Pa. or Aquacoat.™. as supplied by FMC Corporation, Philadelphia, Pa.), nitrocellulose, polylactic acid, polyglycolic acid, polylactide glycolide copolymers, collagen, polyvinyl alcohol, polyvinyl acetate, polyethylene vinylacetate, polyethylene teraphthalate, polybutadiene styrene, polyisobutylene, polyisobutylene isoprene copolymer, polyvinyl chloride, polyvinylidene chloride-vinyl chloride copolymer, copolymers of acrylic acid and methacrylic acid esters, copolymers of methylmethacrylate and ethylacrylate, latex of acrylate esters (such as Eudragit.™. supplied by RohmPharma, Darmstaat, Germany), polypropylene, copolymers of propylene oxide and ethylene oxide, propylene oxide ethylene oxide block copolymers, ethylenevinyl alcohol copolymer, polysulfone, ethylene vinylalcohol copolymer, polyxylylenes, polyalkoxysilanes, polydimethyl siloxane, polyethylene glycol-silicone elastomers, electromagnetic irradiation crosslinked acrylics, silicones, or polyesters, thermally crosslinked acrylics, silicones, or polyesters, butadiene-styrene rubber, and blends of the above.

Preferred materials can include cellulose acetate, copolymers of acrylic acid and methacrylic acid esters, copolymers of methylmethacrylate and ethylacrylate, and latex of acrylate esters. Preferred copolymers can include poly(butyl methacrylate), (2-dimethylaminoethyl)methacrylate, methyl methacrylate) 1:2:1, 150,000, sold under the trademark EUDRAGIT E; poly(ethyl acrylate, methyl methacrylate) 2:1, 800,000, sold under the trademark EUDRAGIT NE 30 D; poly(methacrylic acid, methyl methacrylate) 1:1, 135,000, sold under the trademark EUDRAGIT L; poly(methacrylic acid, ethyl acrylate) 1:1, 250,000, sold under the trademark EUDRAGIT L; poly(methacrylic acid, methyl methacrylate) 1:2, 135,000, sold under the trademark EUDRAGIT S; poly (ethyl acrylate, methyl methacrylate, trimethylammonioethyl methacrylate chloride) 1:2:0.2, 150,000, sold under the trademark EUDRAGIT RL; poly(ethyl acrylate, methyl methacrylate, trimethylammonioethyl methacrylate chloride) 1:2:0.1, 150,000, sold as EUDRAGIT RS. In each case, the ratio x:y:z indicates the molar proportions of the monomer units and the last number is the number average molecular weight of the polymer. Especially preferred are cellulose acetate containing plasticizers such as acetyl tributyl citrate and ethylacrylate methylmethacrylate copolymers such as Eudragit NE.

The foregoing materials for use as the barrier layer can be formulated with plasticizers to make the barrier layer suitably deformable such that the force exerted by the expandable layer will collapse the compartment formed by the barrier layer to dispense the liquid, active agent formulation. Examples of typical plasticizers are as follows: polyhydric alcohols, triacetin, polyethylene glycol, glycerol, propylene glycol, acetate esters, glycerol triacetate, triethyl citrate, acetyl triethyl citrate, glycerides, acetylated monoglycerides, oils, mineral oil, castor oil and the like. The plasticizers can be blended into the material in amounts of 10-50 weight percent based on the weight of the material.

The various layers forming the barrier layer, expandable layer and semipermeable layer can be applied by conventional coating methods such as described in U.S. Pat. No. 5,324,280. While the barrier layer, expandable layer and semipermeable wall have been illustrated and described for convenience as single layers, each of those layers can be composites of several layers. For example, for particular applications it may be desirable to coat the capsule with a first layer of material that facilitates coating of a second layer having the permeability characteristics of the barrier layer. In that instance, the first and second layers comprise the barrier layer. Similar considerations would apply to the semipermeable layer and the expandable layer.

The exit orifice can be formed by mechanical drilling, laser drilling, eroding an erodible element, extracting, dissolving, bursting, or leaching a passageway former from the composite wall. The exit orifice can be a pore formed by leaching sorbitol, lactose or the like from a wall or layer as disclosed in U.S. Pat. No. 4,200,098. This patent discloses pores of controlled-size porosity formed by dissolving, extracting, or leaching a material from a wall, such as sorbitol from cellulose acetate. A preferred form of laser drilling is the use of a pulsed laser that incrementally removes material from the composite wall to the desired depth to form the exit orifice.

Other approaches to achieving controlled release of drugs from oral dosage forms are known in the art. For example, diffusion systems such as reservoir devices and matrix devices, dissolution systems such as encapsulated dissolution systems (including, for example, "tiny time pills") and matrix dissolution systems, combination diffusion/dissolution systems and ion-exchange resin systems are known and are disclosed in Remington's Pharmaceutical Sciences, 1990 ed., pp. 1682-1685. we need to also introduce any type of stomach platform that are designed to release drug in the upper gastrointestinal tract. Dosage forms that operate in accord with these other approaches are encompassed by the scope of the disclosure herein to the extent that the drug release characteristics and/or the blood plasma concentration characteristics as recited herein and in the claims describe those dosage forms either literally or equivalently.

Although the invention has been described with respect to various embodiments, it should be realized this invention is also capable of a wide variety of further and other embodiments within the spirit and scope of the appended claims.

EXAMPLES

Example 1

Ascending release profiles of tizanidine are achieved using a trilayer configuration wherein two drug layers (Layer 1 and Layer 2) and one push layer were compressed in an osmotic drug delivery (e.g. OROS®) system. Typically drug layer 1 consists of lower concentration of the active ingredient than that in layer 2.

Layer 1 is manufactured by charging 106.2 g of tizanidine hydrochloride, 1160.3 g of polyethylene oxide (average molecular weight 200K), 75 g of povidone, 150 g of sodium chloride and 0.8 g of ferric oxide into the bowl of a stand mixer. The dry components are pre-blended. Ethyl alcohol is slowly charged into the bowl while mixing. The wet granulation is then sized with a 16-mesh screen, dried at ambient conditions until an acceptable amount of ethyl alcohol remains and then is sized again. Stearic acid is sieved through a 40-mesh, and butylated hydroxytoluene (BHT) is sieved through a 20-mesh screen. Next 7.5 g of stearic acid and 0.3 g of BHT are combined and mixed in a blender.

Drug layer 2 is prepared in a similar fashion as drug layer 1 using 354.2 g of tizanidine hydrochloride, 1062.3 g of polyethylene oxide (average molecular weight of 200K), 75 g of povidone and 0.8 g of ferric oxide (red), 7.5 g of sieved stearic acid and 0.3 g of sieved BHT.

Next, a push composition is prepared as follows: first, a binder solution is prepared. 27.3 kg of polyvinylpyrrolidone identified as K29-32 having an average molecular weight of 40,000 is dissolved in 182.7 kg of water. Then, 89.60 kg of sodium chloride and 4.48 kg of green iron oxide are sized using a mill. Then, the screened materials and 330.16 kg of Polyethylene oxide (approximately 7,000,000 molecular weight) are added to a fluid bed granulator bowl. The dry materials are fluidized and mixed while 172.32 kg of binder solution is sprayed onto the powder. The granulation is dried in the fluid-bed chamber to an acceptable moisture level. The coated granules are sized using a mill with a 7-mesh screen. The granulation is transferred to a tote tumbler, mixed with 224 g of butylated hydroxytoluene and lubricated with 1200 g stearic acid. Alternatively similar granulations can be made using other techniques that are well known in the art, including dry or wet granulation methods (e.g. fluid bed granulations, roller compaction, direct compression).

Next, the drug and push compositions are compressed into tri-layer tablets. First, 82 mg of the drug granulation layer 1 is added to the die cavity and is pre-compressed. Next, 82 mg of the drug granulation layer 2 is added to the die cavity and is pre-compressed. Finally, 125 mg of the push layer is added to the die cavity, and the layers are compressed in a $\frac{7}{32}$" diameter, longitudinal, deep concave, tri-layer arrangement.

A sub-coat solution comprising of 840 g of hydroxypropyl cellulose and 360 g of povidone in 18.8 kg of ethyl alcohol is prepared and used for coating the tri-layer tizanidine tablets. The subcoat is sprayed onto and around the tri-layered tizanidine drug delivery systems in a pan coater until approximately 20 mg of subcoat is applied onto each system.

A membrane coating mixture comprising of 1,486 g of cellulose acetate and 15 g of polyethylene glycol 3350 in 27.1 kg of acetone and 1,426 g of water is prepared and used for coating the subcoated tri-layer tizanidine tablets. The wall forming composition is sprayed onto and around the subcoated tri-layered tizanidine drug delivery systems in a pan coater until approximately 25 mg of membrane is applied onto each system.

Next, two 25 mil (0.64 mm) orifices are laser drilled through the semi-permeable membrane. The drilled cores were dried in an oven for approximately 72 hours at 45° C. and 45% RH.

The dosage forms produced by this method are designed to deliver 22 mg of tizanidine in an ascending pattern with a duration of approximately 13 hours. Alternatively, different doses of tizanidine (4 mg- 32 mg) can be delivered using the same tri-layered core configuration by (a) changing the API concentration in the drug layers; (b) changing the drug layer (layer 1 or 2) weights; (c) combination of the above. Alternatively, different durations of delivery can be achieved by: (a) changing the coating thickness and weight of the semi-permeable membrane; (b) changing the sodium chloride concentration within the push layer; (c) changing the push layer weight; (d) combination of some or all of the above. The degree of ascent (slope) in these systems can be changed by changing the concentration of sodium chloride in layer 1 and/or by changing the drug concentration gradient in layers 1 and 2.

The above tri-layer example is manufactured using tizanidine hydrochloride, but other pharmaceutically acceptable salts of tizanidine (e.g. sulfate, succinate, hemisuccinate sesquihydrate, citrate, acetate, etc) can be used to make a system that releases the drug in an ascending fashion.

Example 2

Results from Ascending Release Profile

In vitro results: The 22 mg ascending profile systems generated above are subjected to release rate testing using pH 2.0 media. Typical results are shown in FIG. 3.

Example 3

Evaluation of Various Tizanidine Salt Forms for OROS Ascending Profile Systems

Various salt forms of tizanidine (hydrochloride, hemisuccinate sesquihydrate, sulfate, succinate, hemisulfate hemihydrate) are used to make tri-layer tablets in an osmotic drug delivery (e.g. OROS®) system that releases tizanidine in an ascending profile. The drug concentration is adjusted for the molecular weights of the corresponding tizanidine salts to achieve a dose of 22 mg of tizanidine base. An example for manufacturing the tri-layer tablet with tizanidine hemisuccinate sesquihydrate (Tn HSSH) is given below.

Example 3

Tri-layer systems containing tizanidine hemisuccinate sesquihydrate are made as follows: Ten grams of drug layer 1 is prepared in a beaker scale by charging 8.29 g of Tn HSSH, 76.19 g of polyethylene oxide (average molecular weight 200K), 10 g of sodium chloride, 5 g of povidone and 0.05 g of iron oxide into a beaker and is dry blended. Ethyl alcohol is slowly charged into the beaker while stirring. The wet granulation dried at ambient conditions until an acceptable amount of ethyl alcohol remains. The dried granulation is sieved using a 16-mesh screen and isblended with 0.5 g stearic acid and 0.02 g BHT.

Next, drug layer 2 is prepared in a similar manner except that the composition consists 27.64 g of tizanidine hemisuccinate sesquihydrate, 66.79 g of polyethylene oxide (average molecular weight 200K), 5 g of povidone, 0.05 g of ferric oxide, 0.5 g of stearic acid and 0.02 g of BHT.

Next, a push composition is prepared as follows: first, a binder solution is prepared. 27.3 kg of polyvinylpyrrolidone identified as K29-32 having an average molecular weight of 40,000 is dissolved in 182.7 kg of water. Then, 89.60 kg of sodium chloride and 4.48 kg of green iron oxide are sized using a mill. Then, the screened materials and 330.16 kg of Polyethylene oxide (approximately 7,000,000 molecular weight) are added to a fluid bed granulator bowl. The dry materials are fluidized and mixed while 172.32 kg of binder solution is sprayed onto the powder. The granulation is dried in the fluid-bed chamber to an acceptable moisture level. The coated granules are sized using a mill with a 7-mesh screen. The granulation is transferred to a tote tumbler, mixed with 224 g of butylated hydroxytoluene and lubricated with 1200 g stearic acid.

Alternatively similar granulations can be made using other techniques that are well known in the art, including dry or wet granulation methods (e.g. fluid bed granulations, roller compaction, direct compression).

Next, the drug and push compositions are compressed into tri-layer tablets. First, 82 mg of the drug granulation layer 1 is added to the die cavity and is pre-compressed. Next, 82 mg of the drug granulation layer 2 is added to the die cavity and is pre-compressed. Finally, 125 mg of the push layer is added to the die cavity, and the layers are compressed in a $\frac{7}{32}$" diameter, longitudinal, deep concave, tri-layer arrangement.

A sub-coat solution comprising 840 g of hydroxypropyl cellulose and 360 g of povidone in 18.8 kg of ethyl alcohol is prepared and used for coating the tri-layer tizanidine tablets. The subcoat is sprayed onto and around the tri-layered tizanidine drug delivery systems in a pan coater until approximately 20 mg of subcoat is applied onto each system.

A membrane coating mixture comprising of 1,486 g of cellulose acetate and 15 g of polyethylene glycol 3350 in 27.1 kg of acetone and 1,426 g of water is prepared and used for coating the subcoated tri-layer tizanidine tablets. The wall forming composition is sprayed onto and around the subcoated tri-layered tizanidine drug delivery systems in a pan coater until approximately 25 mg of membrane is applied onto each system.

Next, two 25 mil (0.64 mm) orifices are laser drilled through the semi-permeable membrane. The drilled cores were dried in an oven for approximately 72 hours at 45° C. and 45% RH.

Example 4

Results from Ascending Profile Cores of Various Tizanidine Salts in Different Media In vitro results: The 22 mg ascending profile systems using tizanidine hemisuccinate sesquihydrate featured above are subjected to release rate testing using pH 2.0 media. Release rate results of this and other tizanidine salt forms are shown in FIG. 4.

Example 5

Study C-2006-015, titled "Pharmacodynamic and Pharmacokinetic Evaluation of IR Tizanidine and OROS® Tizanidine", conducted in healthy subjects, compared the pharmacodynamics (cardiovascular, sedative and cognitive effects) of two pilot release profiles of OROS® Tizanidine HCl (Zero-order and Ascending Profile) to IR tizanidine tablets and placebo. An additional objective of the study was to evaluate the pharmacokinetic bioavailability of the two OROS® Tizanidine HCl release profiles relative to IR tizanidine.

In this single-center, double-blind, placebo-controlled, four-period, four-treatment crossover study, each subject was randomized to receive the following 4 treatments with a washout period of a minimum of 6 days and not more than 15 days between treatments:

Treatment A: Three doses of IR tizanidine 8 mg tablet given at 0, 6, and 12 hours Treatment B: Single dose of OROS® Tizanidine HCl 24 mg Zero-order release profile
Treatment C: Single dose of OROS® Tizanidine HCl 24 mg Ascending release profile
Treatment D: Placebo Both the OROS® Zero-order and Ascending release profiles (Treatment B and C) were designed to deliver 22 mg of tizanidine (free base equivalent) in a zero-order or ascending fashion, respectively, over an extended period of time. A single 2 mg IR tizanidine tablet, given simultaneously with the OROS® treatments (total dose 24 mg), was intended to mimic the IR overcoat that is designed for use in future OROS® Tizanidine trials.

OROS® Tizanidine Zero-order profile (Treatment B) was designed to deliver 22 mg of tizanidine (free base equivalent) in a zero-order fashion over extended period of time. The nominal release duration of the system (T90) was 22 hours and the average release rate was approximately 1 mg/hr.

OROS® Tizanidine Ascending profile (Treatment C) was designed to deliver 22 mg of tizanidine (free base equivalent) in a controlled ascending pattern over extended period of time. The nominal release duration of the OROS® Ascending system (T90) was 12 hours and the release rate steadily increased during the first 10 hours of release, ranging from approximately 0.2 to approximately 2.4 mg/hr.

To assess the pharmacodynamic effects of OROS® Tizanidine HCl, the following measures were administered at specified time points which corresponded to the expected time for tizanidine plasma peak and trough concentrations:

Karolinska Sleepiness Scale (KSS) administered at pre-dose, 1.5, 4, 7, 11, 13, and 23 hours following the morning dose Cognitive Drug Research (CDR) tests conducted at check-in (2 practice tests), pre-dose, 1.5, 4, 7, 11, 13, and 23 hours following the morning dose.

Venous blood samples were collected from each subject for measurement of tizanidine and tizanidine metabolites (3, 4 and 10) at 0 (pre-dose), 0.5, 1, 1.5, 2, 4, 6, 7, 8, 11, 13, 16, 22, 23, 24, and 28 hours following the morning dose in each treatment period.

Pharmacokinetic parameters determined from plasma concentration data of tizanidine and tizanidine metabolites included $C_{max}$, $T_{max}$, $t_{1/2}$, and $AUC_{0-28h}$.

Safety measures were collected and included the following:

Orthostatic assessments obtained at screening, check-in, pre-dose, 0.5, 1.5, 4, 5, 6, 7, 11, 12, 13, 23, and 28 hours (discharge)

AEs and concomitant medications collected and reported throughout the duration of the study Laboratory assessments (complete blood count, serum chemistry, and urinalysis) checked at screening, check-in of each treatment period, and study termination Physical exams performed at screening and study termination Urine drug screen performed at screening and check-in
Alcohol analysis completed at check-in
12-lead electrocardiogram (ECG) completed at screening and at study termination Vital signs (blood pressure, heart rate, and respiratory rate) performed at screening, check-in and 0 (pre-dose), 1, 2, 3, 4, 6, 8, 12, 24 and 28 hours post morning dose and at study termination Serum pregnancy tests at screening and a urine pregnancy test at check-in for women of child-bearing potential This Phase 1 study enrolled 32 nonsmoking healthy subjects aged 18-45 with a body mass index (BMI) between 18-29 kg/m². Subjects were required to use a medically acceptable method of birth control throughout the study and for 90 days following study completion. Exclusion criteria included the absence of orthostatic hypotension (supine-to-standing blood pressure decrease >20 mm Hg systolic or >10 mm Hg diastolic after standing for 3 minutes), systolic blood pressure (SBP) <100 mm Hg, symptoms of lightheadedness or fainting upon standing, resting heart rate (HR) <45 beats per minute (bpm) or >100 bpm. Subjects with a history of significant drug or alcohol abuse, drug allergies or sensitivities, or consumption of >450 mg/day of caffeine were excluded.

Pharmacokinetics

To follow are preliminary PK results from the Phase 1 study conducted in healthy subjects. Table 0-1 summarizes the mean pharmacokinetics parameters for tizanidine following administration of IR tizanidine tablets (8 mg given at 0, 6, and 12 h), OROS® Tizanidine HCl Zero-order, 24 mg and OROS® Tizanidine HCl Ascending, 24 mg. The OROS® treatments included a 2 mg immediate-release tablet encapsulated with the appropriate 22 mg OROS® tablet. Elimination half-life ($t_{1/2}$) values for the IR treatment were estimated following the 0-hour dose. Half-life values could not be estimated for the OROS® formulations because of the short duration of plasma sampling. Consistent with reports in the literature, the mean $t_{1/2}$ following IR tizanidine tablets was 1.7±0.4 hours. Median time to peak tizanidine plasma concentrations for the IR tablets, OROS® Zero-order and OROS® Ascending profiles were approximately 1.5, 7.0, and 11 hours, respectively. Peak concentrations following the OROS® formulations were lower than those following the IR treatment. The OROS® Zero-order profile resulted in approximately constant tizanidine concentrations. The OROS® Ascending profile resulted in a slightly ascending profile with peak plasma concentrations that were intermediate between the OROS® Zero-order profile and the IR regimen. The OROS® Ascending treatment resulted in complete bioavailability compared to the IR treatment. The lower mean relative bioavailability for the OROS® Zero-order profile (76.7%) may in part be due to the potential defecation of the OROS® system prior to the end of the 22-hour delivery duration.

TABLE 0-1

Mean (SD) Pharmacokinetic Parameters for Tizanidine

| | Immediate-Release Tizanidine (n = 22) | OROS ® Zero-Order Profile Tizanidine HCl (n = 23) | OROS ® Ascending Profile Tizanidine HCl (n = 23) |
|---|---|---|---|
| $C_{max}$ (ng/mL) | 4.3 ± 2.7 | 1.6 ± 1.1 | 2.2 ± 1.3 |
| $T_{max}$ (h)[a, b] | 1.5 | 7.0 | 11.0 |
| $t_{1/2}$ (h)[b] | 1.8 ± 0.4 | — | — |
| $AUC_{0-28}$ (ng · h/mL) | 31.1 ± 21 | 22.7 ± 13 | 29.0 ± 19 |
| F (%)[c] | — | 76.7 ± 35 | 115.7 ± 64 |

[a]median
[b]n = 19
[c]n = 22; relative to IR tizanidine
Source: Study C-2006-015; Table 11.1.2.1, 11.1.2.2, and 11.1.2.4

Pharmacodynamics

Preliminary pharmacodynamic data from the Phase 1 clinical study is presented below. The Karolinska Sleepiness Scale (KSS), a nine-point subjective scale used to measure sleepiness, and a battery of computerized CDR cognitive tasks was administered. The CDR tasks included:

Simple Reaction Time
Digit Vigilance Task
Choice Reaction Time (CRT)
Tracking
Digital Symbol Substitution Test (DSST)

Additionally, two composite scores, Power of Attention (a measurement of the intensity of concentration at a particular moment) and Continuity of Attention (a measurement of sustained attention and avoidance of error), were calculated from the scores of the individual CDR tasks.

The data indicated that IR tizanidine 8 mg tablets caused subjective sleepiness (KSS) and objective cognitive impairment at 1.5 hours (Power of Attention and Continuity of Attention composite scores), which resolved by 7 hours. These effects with IR tizanidine were therefore only seen following the first dose, with subsequent doses at 6 and 12 hours not producing clear subjective or objective sedation. Of note, the peak decrement seen in Power of Attention composite scores with IR tizanidine 8 mg (189 msec) is comparable to that seen previously with this dose with administration of tablets or capsules in the fed or fasted state.

For both OROS® Tizanidine HCl treatments, subjective assessment of sedation (sleepiness) as measured by KSS at 1.5 hours was comparable in magnitude to that seen with the first dose of IR tizanidine 8 mg, with statistically significant sleepiness observed at 7 hours. However, for the OROS® Zero-order formulation, at 7 hours, this increased subjective sleepiness was not accompanied by impairment in the Continuity of Attention composite scores, although impairment was seen in the Power of Attention scores. Neither subjective nor objective sedation was seen at the other time points for OROS® Zero-order.

For the OROS® Ascending treatment, objective cognitive impairment was seen in both the Power of Attention composite scores and Continuity of Attention composite scores at 7 hours as well as for Continuity of Attention composite scores at the 13-hour time point. Of note, however, placebo treatment showed an improvement in Power of Attention composite scores at 7 hours. Thus, the effects noted for impairment of Power of Attention composite scores for the OROS® formulations may be due to improvement in the placebo performance rather than to an effect of the active treatment. Consistent with this, although the IR tizanidine-treated group did not show subjective sleepiness (KSS), they also exhibited impaired Power of Attention composite scores at the 7-hour time point.

The clinical relevance of these effects on Power of Attention may be put in perspective by comparing them to alcohol, a drug widely known to impair cognition in a dose-related fashion. Peak impairment in Power of Attention with doses of 0.5-0.7 g/kg alcohol typically result in a decrement of about 150 msec in Power of Attention compared to baseline. Importantly, the peak decrement seen in Power of Attention with IR tizanidine 8 mg of 189 msec seen at 1.5 hours was comparable to than seen with a high dose of alcohol (0.7 g/kg). In comparison, OROS® Tizanidine produced peak decline in Power of Attention of 77 msec at 1.5 hours and 79 msec at 13 hours with the Zero-order and Ascending profile, respectively. Neither of these decrements was statistically significantly different from placebo and was only slightly greater than would be expected with placebo.

Adverse Events

Final data are not available for this study and the following represents preliminary observations. A full safety evaluation will be included in the IND submission. No serious AEs were reported during the study. Nine subjects in total withdrew from the study. AEs that led to discontinuation included hypotension, elevated gamma glutamyl-transpeptidase (GGT), somnolence, infusion site pain, tachycardia, nausea and vomiting. Across treatment groups, most AEs were reported as either mild or moderate. The most common AEs reported were somnolence, fatigue and headache. In general, however, AEs associated with known pharmacodynamic effects of tizanidine (e.g., somnolence, dizziness, dry mouth and hypotension) were reported in fewer patients receiving either OROS® formulations compared to IR tizanidine.

Adverse events rated as moderate in severity included somnolence, fatigue, lethargy, hypotension, dizziness and pain. Reports of somnolence, lethargy, and fatigue were rated as moderate in more patients receiving IR tizanidine than in patients taking either OROS® formulations.

Overall, mean orthostatic vital signs were comparable across treatment groups. Although some individual vital sign measurements were considered clinically relevant, these values normalized by the end of each treatment period without clinical intervention. In general, decrements in blood pressure readings from baseline were in no instances greater during treatment with either OROS® formulation compared to IR tizanidine.

In general, mean laboratory values were similar at the end of the study assessment compared to baseline values. No significant changes in values were noted across treatment groups. All mean values were also within normal limits except for a slight elevation in phosphate levels in both screening and termination laboratories in almost all subjects, which were not considered clinically significant by the investigator.

Most of the individual blood chemistry, hematology, and urinalysis values were also within normal ranges. Although some individual laboratory results fell outside the normal limit range, the investigator judged these values not to be clinically significant. Only one abnormal laboratory value was reported as an AE (elevated liver function tests). This patient had an elevated GGT to 41 IU/L (normal range 9-36 IU/L) on study termination, however this parameter normalized upon follow-up.

What is claimed is:

1. A method for treating a patient suffering from spasticity comprising orally administering to the patient an osmotic dosage form comprising a core comprising
    a first layer of tizanidine succinate,
    a second layer of tizanidine succinate, and
    a expandable push layer; and
    a semi-permeable membrane,
wherein the tizanidine succinate is released from the dosage form in manner such that the concentration of tizanidine in the plasma of the patient substantially ascends over a period of 8 hours following administration of the dosage form and the concentration of tizanidine in the plasma of the patient is between 1-4 ng/mL.

2. The method of claim 1, wherein the dosage form provides a peak concentration of tizanidine succinate in the plasma of the patient of between 1.6-3.2 ng/ml.

3. An osmotic dosage form comprising
    a core comprising
        a first layer of tizanidine succinate comprising between 5 and 25% of tizanidine succinate,
        a second layer of tizanidine succinate comprising between 75 and 95% tizanidine succinate, wherein the first layer of tizanidine succinate is substantially released within 3 hours of administration of the dosage form and the second layer of tizanidine succinate is substantially released over a period of 1-14 hours of administration of the dosage form, and an expandable push layer; and
a semi-permeable membrane,
wherein the tizanidine succinate is released from the dosage form in manner such that the concentration of tizanidine in the plasma of the patient substantially ascends over a period of 8 hours following administration of the dosage form.

4. The method of claim 1 wherein the first layer of tizanidine succinate is substantially released within 3 hours of administration of the dosage form and the second layer of tizanidine succinate is substantially released over a period of 1-14 hours of administration of the dosage form.

5. The method of claim 1 wherein the osmotic dosage form further comprises a sub-coating surrounding the core, and the semi-permeable membrane surrounds the sub-coating.

6. The method of claim 5 wherein the sub-coating comprises an orifice.

7. The method of claim 1 wherein the semi-permeable membrane comprises an orifice.

8. The osmotic dosage form of claim 3 wherein administration of the dosage form to a patient provides a peak concentration of tizanidine in the plasma of the patient of between 1-4 ng/ml.

9. The osmotic dosage form of claim 3 wherein administration of the dosage form to a patient provides a peak concentration of tizanidine in the plasma of the patient of between 1.6-3.2 ng/ml.

10. The osmotic dosage form of claim 3 further comprising a sub-coating surrounding the core, wherein the semi-permeable membrane surrounds the sub-coating.

11. The osmotic dosage form of claim 10 wherein the sub-coating comprises an orifice.

12. The osmotic dosage form of claim 3 wherein the semi-permeable membrane comprises an orifice.

* * * * *

UNITED STATES PATENT AND TRADEMARK OFFICE
CERTIFICATE OF CORRECTION

PATENT NO. : 8,524,749 B2 Page 1 of 1
APPLICATION NO. : 12/014980
DATED : September 3, 2013
INVENTOR(S) : Bull et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 848 days.

Signed and Sealed this

Twenty-third Day of May, 2017

Michelle K. Lee
*Director of the United States Patent and Trademark Office*